United States Patent
Fu et al.

(10) Patent No.: US 6,635,490 B1
(45) Date of Patent: Oct. 21, 2003

(54) PROCEDURE FOR THE SIMULTANEOUS QUANTITATIVE AND QUALITATIVE ANALYSIS OF BOTH FLAVONOID GLYCOSIDES AND STEROIDAL GLYCOSIDES

(75) Inventors: Kejian Fu, Mississauga (CA); Maciej A. Kaminski, Mississauga (CA); Jessica Liu, Brampton (CA)

(73) Assignee: Noble Laboratories, Brampton (CA)

( * ) Notice: Subject to any disclaimer, the term of this patent is extended or adjusted under 35 U.S.C. 154(b) by 0 days.

(21) Appl. No.: 09/578,649

(22) Filed: May 25, 2000

(51) Int. Cl.$^7$ ............................................. G01N 33/00
(52) U.S. Cl. ........................ 436/94; 536/18.5; 536/128
(58) Field of Search .......................... 436/94; 536/18.5, 536/128

(56) References Cited

U.S. PATENT DOCUMENTS

| | | | | |
|---|---|---|---|---|
| 2,681,907 | A | * 6/1954 | Wender | 536/8 |
| 4,238,483 | A | 12/1980 | Frazier | |
| 4,428,876 | A | * 1/1984 | Iwamura | 530/370 |
| 4,968,787 | A | 11/1990 | Inada et al. | |
| 5,679,806 | A | * 10/1997 | Zheng et al. | 549/459 |
| 5,698,526 | A | 12/1997 | Deninno | |
| 5,955,269 | A | 9/1999 | Ghal et al. | |
| 6,252,093 | B1 | * 6/2001 | McMorris | 435/6 |
| 6,329,146 | B1 | * 12/2001 | Crooke et al. | 435/6 |

OTHER PUBLICATIONS

Takeda, K., et al., Studies on the Steroidal Components of Domestic Plants—XLVI Constituents of Hosta Species (3) $\Delta^{25(27)}$—and the Saturated 25D– or 25L–Sapogenins. Journal of Chemical Society C (1967)(9): 876–882.

Takeda, K., et al, Studies on Biochemical Transformation of Plant Steroids. Part II. Biochemical Conversion of Gitogen into 12–Oxygenated Sapogenins in Hosta Kivosumiensis. Chemical and Pharmaceutical Bulletin (1968) 16(2): 275–279.

Mimaki, Y., e tal., Steroidal Saponins from the Underground Parts of Hosta Longpipes and Their Inhibitory Activity on Tumor Promoter–Induced Phospholipid Metabolism. Chemical and Pharmaceutical Bulletin (1995) 43(7): 1190–1196.

Mimaki, Y., et al., Steroidal Saponins from Hosta Longpipes and Their Inhibitory Activity on Tumor Promoter–Induced Phospholipid Metabolism of HeLa Cells. Phytochemistry (1996) 42(4): 1065–1070.

Mimaki, Y., et al., Steroidal glycosides from the Underground Parts of Hosta Plantaginea Var. Japonica and Their Cytostatic Activity on Leukaemia HL–60 Cells. Phytochemistry (1997) 44(2): 305–310.

(List continued on next page.)

Primary Examiner—Jill Warden
Assistant Examiner—Monique T. Cole
(74) Attorney, Agent, or Firm—Caesar, Rivise, Bernstein, Cohen & Pokotilow, Ltd.

(57) ABSTRACT

A single rapid procedure for the quantitative and qualitative analysis of flavonoid glycosides and steroidal glycosides, in natural products, has been developed. The material is extracted with aqueous solutions of polar organic solvents in an ultrasonic bath. Interfering compounds are removed by pre-purification procedures prior to instrumental analysis by High Pressure Liquid Chromatography with Negative Ion Electrospray Mass Spectrometric Detection and on-line Diode Array Ultraviolet-Visible Spectroscopy. The analysis of flavonoid and steroidal glycosidic compounds in HOSTA leaves served as a model system.

30 Claims, 13 Drawing Sheets

OTHER PUBLICATIONS

Mimaki, Y., et al., Steroidal Saponins from the Rhizomes of Hosta Sieboldii and The Cytostatic Activity On HL–60 Cells. Phytochemistry (1998)48(8) 1361:1369.

Ochi, M., et al., Steroid Saponin from Hosta and Antimicrobial and Antitumor Agents Containing It. JP 10 114,791 [98 114,791], May 6, 1998, Appl. 96/270,292, Oct. 11, 1996; 12 pp; CA 129: 32293w.

Ochi, M., et al., Novel Steroidal Saponin and Antimicrobial Agents and Antitumor Agents Cotnaining It. JP 10 158,295 [98 158, 295], Jun. 16, 1998, Appl. 96/320, 142, Nov. 29, 1996; 12 pp; CA 129:113511t.

Shibata, S., The Chemistry of Chinese Drugs. American Journal of Chinese Medicine (1079( 7(2): 103–141.

Hartwell, J.L., et al., Antineoplastic Principles in Plants: Recent Developments in the Field. Advances in Pharmacology (1969) 1:117–209.

Rao, A.V., et al., Anticarcinogenic Effects of Saponins and Phytosterols. American Chemical Society Symposium Series (1997) 662: 313–324.

Hartwell, J.L., Types of Anticancer Agents Isolated from Plants. Cancer Treatment Reports (1970)60(8): 1031–1067.

Hutabarat, L.S., et al., Development and Validation of an Isocratic High–Performance Liquid Chromatographic Method for Quantitative Determination of Phytoestrogens in Soya bean. Journal of Chromatographs A (1998( 795: 377–382.

Wolfender, J., et al., Comparison of Liquid Chromatography/Electrospray, Atmospheric Pressure Chemical Ionization, Thermospray and Continuous–flow Fast Atom Bombardment Mass Spectrometry for the Determination of Secondary Metabolities in Crude Plant Extracts. Journal of Mass Spectrometry and Rapid Communications in Mass Spectrometry (1995) (Special Issue): S35–S46.

Maillard, M.P., et al., Use of Liquid Chromatography—Thermospray Mass Spectrometry in Phytochemical Analysis of Crude Plant Extracts. Journal of Chromatography (1993) 647:147–154.

Games, D.E. Combined High Performance Liquid Chromatography Mass Spectrometry. Biomedical Mass Spectrometry (1981)8(9): 454–462.

Vaccaro, W.D., et al., Sugar–Substituted 2–Azetidinone Cholesterol Absorption Inhibitors: Enhanced Potency by Modification of the Sugar. Bioorganic & Medicinal Chemistry Letters (1998)8: 313–318.

Price, K.R., et al., the Chemistry and Biological Significance of Saponins in Foods and Feedingstuffs. Critical Reviews in Food Science and Nutrition (1987)26(1):27–135.

Fang, S., et al., Rapid Analysis of Steroidal Saponin Mixture Using Electrospray Ionization Mass Spectrometry Combined with Sequential Tandem Mass Spectrometry. Rapid Communications in Mass Spectrometry (1998) 12:589–594.

Maillard, M.P., e tal., Determination of Saponins in Crude Plant Extracts b Liquid Chromatography–Thermospray Mass Spectrometry. Journal of Chromatography (1993) 647: 137–146.

Lee, M., et al., Analysis of Saponins from Black Bean by Electrospray Ionization and Fast Atom Bombardment Tandem Mass Spectrometry. Journal of Mass Spectrometry (1999) 34: 804–812.

Van Setten, D.C., et al., Multiple–Stage Tandem Mass Spectrometry for Structural Characterization of Saponins. Analytical Chemistry (1998) 70(20):4401–4409.

Hostettmann K., et al., Saponins—Chemistry and Pharmacology of Natural Product, Cambridge University, Cambridge (1995).

Fuzzati, N., et al., Identification of Soyasaponins by Liquid Chromatography—Thermospray Mass Spectrometry. Journal of Chromatograph A (1997) 777:233–238.

Mostad, H. B., et al., Separation and Characterization of Oleanene–type Pentacyclic Triterpenes from Glpsophila Arrostii by Liquid Chromatography–Mass Spectrometry. Journal of Chromatography (1087) 396:157–168.

Hardman, R., Board of Pharmaceutical Sciences (editor), Conception and Contraception, Exerpta Medica, Amsterdam, (1975) p. 60.

Pietta P., Flavonoids in medicinal plants, Antioxidant Health Dissertation (1998), 7 (Flavonoids in Health and Disease), 61–100.

Pietta P.G., et al., Fitomedicine e Nutrienti, Verona: Ricchiuto GM, (1996).

Bors, W., et al. Radical Chemistry of Flavonoid Antioxidants. Antioxidants in Therapy and Preventative Medicine (1990) 264:165–170.

Budzianowski, J., et al., Studies on Antioxidative Activity of Some C–glycosylfavones. Polish Journal of Pharmacology and Pharmacey (1991)43:395–401.

Lonchampt, M. et al., Protective Effect of a Purified Flavonoid Fraction against Reactive Oxygen Radicals. Arzneimittelforchung (1989)39(8):882–885.

Saija, A., et al., Flavonoids as Antioxidant Agents:Importance of their Interaction with Biomembrances. Free Radical Biology & Medicine (1995)19(4): 481–486.

Von Wacker, A., Antivirale Wirkung on Pfanzeninhaltsstoffen. Arzneimittelforschung (1978)28(3):347–350.

Pietta P. G., et al., Fitomedicine e Nutrieti. Verona: Ricchiuto GM, (1996).

Pathak D., et al., Fitoterapia (1991) 62:371.

Dawidar, A.M., et al., Mass Spectra of Steroid Saponins. Journal of Pharmaceutical Sciences (1974) 63: 140–142.

Harborn and Williams. the Flavonoids. Ed. Harborn, J.B., et al., Chapman and Hall, (1975): 376–441.

Franski, R., et al., Application of mass spectrometry to structural identification of flavonoid monoglycosides isolated from shoot of lupin (*Lupinus luteus L.*) Acta Biochimica Polonica (1999)46(2)459–473.

Nakaori, T., et al, Journal of Pharmaceutical Sciences Japan. (1956) 76:323.

Lunte, S.M., Structural Classification of Flavonoids in Beverages by Liquid Chromatography with Ultraviolet–Visible and Electrochemical Detection. Journal of Chromatography (1987) 384:371–382.

Tsuchiya, H., High–performance Liquid Chromatographic Analysis of Polyhydroxyflavones Using Solid–phase Borate–complex Extraction. Journal of Chromatography B (1998) 720:225–230.

Guinaudeau, H., et al., Phytochemistry (1981)20:1113.

Hosny, M., Novel Isoflavone, Cinnamic Acid, and Triterpenoid Glycoides in Soybean Molasses. Journal of Natural Products (1999) 62(6)853–858.

Harborn, J. B. et al. Flavone and Flavonol Glycosides. Flavonoids: Advances in Research (1082)261–311. Editor: Harborne J.

Wolf, W.J., et al, Journal of American Oil Chemists Society. (1970) 47:89.

Stewart et al., Biochemical Systems Ecology. (1980) 8:119.

Galensa R., et al., Analyse von Flavonoidgylcosiden durch Hochdruck–Flusskeits—chromatographihe (19789) 166:355–358.

Domon, B., Jurnal of Chromatography (1984)315:441.

Hasler, A., et al., High–performance Liquid Chromatogrpahic Determination of Five Widespread Flavonoid Aglycones, Journal of Chromatography (1990)508:236–240.

$39^{th}$ Annual Congress on Medicinal Plant Research Sep. 1991.

Iida, J., et al., Application of Thermospray Liquid Chromatography/mass Spectrometry to Analysis of Glycosides. Analytical Sciences (1991)(Supplement): 963–966.

Maillard, M.P., et al., Thermospray LC–MS Analysis of Saponins in Crude Plant Extracts. Planta Medica (1992) 58 (Supplement Issue 1): A 673.

Wolfender, J.L., et al., Liquid Chromatographic–Thermospary Mass Spectrometric Analysis of Crude Plant Extracts Containing Phenolic and Terpene Glycosides. Journal of Chromatography (1993) 647: 183–190.

Pietta, P., et al., Thermospray Liquid Chromatography–mass Spectrometry of Flavonal Gylcosides From Medicinal Plants. Journal of Chromatography A (1994)661:121–126.

Wolfender, J.L., et al., Liquid Chromatography Combined With Thermospray and Continuous–Flow Fast Atom Bombardment Mass Spectrometry of Glycosides in Crude Plant Extracts. Journal of Chromatography A (1995) 712:155–168.

Hakkinen, S., et al., High–performance Liquid Chromatography With Electrospray Ionization Mass Spectrometry and Diode Array Ultraviolet Detection in the Identification of Flavonol Aglycones and Glycosides in Berries. Journal of Chromatograph A (1998) 829:91–100.

Schopke,, T., et al., Application of MS–MS for the Rapid, Comparative Analysis of Saponin Mixtures as Exemplified by the Deacylated and Partially Deacylated Triterpenoid Saponins of *Bellis annua*. Planta Medica (1996) 62:336–340.

Mauri, P. L., et al., Liquid Chromatography/Electrospray Ionization Mass Spectrometric Characterization of Flavonal Glycosides in Tomato Extracts and Human Plasma. Rapid Communications in Mass Spectrometry (1999) 13: 924–931.

Stobiecki, M., et al., Detection of Isoflavonoids and their Glycosides by Liquid Chromatography/Electrospray Ionization Mass Spectrometry in Root Extracts of Lupin (*Lupinus albus*). Pytochemical analysis (1999) 10: 198–207.

Gelpi, e., Biomedical and Biochemmical Applications of Liquid Chromatography–Mass Spectrometry. Journal of Chromatography A (1995) 703:59–80.

Watson, D.G., et al., Analysis of Flavonoids in Tablets and Urine by Gas Chromatography/Mass Spectrometry and Liquid Chromatography/Mass Spectrometry. Rapid Communications in Mass Spectrometry (1998) 12: 153–156.

Justesen, U., et al., Quantitative Analysis of Flavonols, Flavanes, and Flavonones in Fruits, Vegetables and Beverages by High–performance Liquid chromatography with Photo–diode array and mass spectrometric detection. Journal of Chromatography (1998) 799: 101–110.

Jiang Su New Medical College (ed.), "Dictionary of traditional Chinese crude drugs", vol. 1, Shanghai Scientific Technologic Publishers, Shanghai, (1977), p. 557.

Budzianowski, J., Kaempferol Glycosides from Hosta Ventricosa. Phytochemistry (1990) 29(1):3463–3467.

* cited by examiner

| NO. | COMPOUND | | COMPOSITIONS IDENTIFIED BY THE APPLICATION OF THE PRESENT REPORT | KAEMPFEROL GLYCOSIDES PREVIOUSLY IDENTIFIED | STEROIDAL GLYCOSIDES PREVIOUSLY IDENTIFIED |
|---|---|---|---|---|---|
| | MASS | COMPOSITION | | | |
| 1 | 594 | (K+2) | X | X #1 | |
| 2 | 610 | (K+2) | X | X #2 | |
| 3 | 726 | (K+3) | X | X #3 | |
| 4 | 756 | (K+3) | X | X #4 | |
| 5 | 756 | (K+3) | X | X #5 | |
| 6 | 772 | (K+3) | X | X #6 | |
| 7 | 886 | (S+3) TIGOGENIN | X | | X (1) |
| 8 | 888 | (K+4) | X | X #7 | |
| 9 | 902 (NEW) | (K+4) | X | | |
| 10 | 918 | (K+4) | X | X #8 | |
| 11 | 932 | (S+3) MANOGENINE | X | | X (2) |
| 12 | 1048 | (S+4) HECOGENIN | X | | X (3) |
| 13 | 1064 | (S+4) MANOGENIN | X | | X (4) |
| 14 | 1066 (NEW) | $(S+H_2O+4)$ TIGOGENIN | X | | |
| 15 | 1226 (NEW) | (S+5) GITOGENIN | X | | |
| 16 | 1244 (NEW) | $(S+H_2O+6)$ GITOGENIN (450) | X | | |
| 17 | 1360 (NEW) | $(S+H_2O+6)$ TIGOGENIN (434) | X | | |
| 18 | 1376 (NEW) | $(S+H_2O+6)$ (450) | X | | |
| 19 | 1390 (NEW) | $(S+H_2O+6)$ TIGOGENIN (434) | X | | |
| 20 | 1406 (NEW) | $(S+H_2O+6)$ GITOGENIN (450) | X | | |

K - KAEMPFEROL
S - SAPOGENINE

FIG. 4

| COMPOUNDS | $R_1$ | $R_2$ | MOLECULAR WEIGHT |
|---|---|---|---|
| #1 | Rha-Glc | H | 594 |
| #2 | Glc-Glc | H | 610 |
| #3 | Xyl-Rha-Glc | H | 726 |
| #4 | Glc-Rha-Glc | H | 756 |
| #5 | Rha-Glc | Glc | 756 |
| #6 | Glc-glc | Glc | 772 |
| #7 | Xyl-Rha-Glc | Glc | 888 |
| #8 | Glc-Rha-Glc | Glc | 918 |

| COMPOUNDS | $R_1$ | $R_2$ | $R_3$ | $R_4$ | $R_5$ | MOLECULAR WEIGHT |
|---|---|---|---|---|---|---|
| (1) | H, H | H | α-L-Rhap | H | H | 886 |
| (2) | O | OH | H | H | Glc | 932 |
| (3) | O | H | H | Xyl | Glc | 1048 |
| (4) | O | OH | H | Xyl | Glc | 1064 |

| NO. | MOLECULAR WEIGHT | AGLYCONE | GLYCOSIDES TYPE | NUMBER |
|---|---|---|---|---|
| 1 | 1066 | (TIGOGENINE + $H_2O$) $C_{27}H_{46}O_4$, MW = 434 | 3 Glc<br>1 Rha | (4) |
| 2 | 1226 | (GITOGENIN) $C_{27}H_{44}O_4$, MW = 432 | 4 Glc<br>1 Rha | (5) |
| 3 | 1244 | (GITOGENIN + $H_2O$), $C_{27}H_{46}O_5$, MW = 450 | 4 Glc<br>1 Rha | (5) |
| 4 | 1360 | (TIGOGENINE + $H_2O$), $C_{27}H_{46}O_4$, MW = 434 | 4 Glc<br>1 Rha<br>1 Xyl | (6) |
| 5 | 1376 | (GITOGENIN + $H_2O$), $C_{27}H_{46}O_5$, MW = 450 | 4 Glc<br>1 Rha<br>1 Xyl | (6) |
| 6 | 1390 | (TIGOGENINE + $H_2O$), $C_{27}H_{46}O_4$, MW = 434 | 5 Glc<br>1 Rha | (5) |
| 7 | 1406 | (GITOGENIN + $H_2O$), $C_{27}H_{46}O_5$, MW = 450 | 5 Glc<br>1 Rha | (6) |
| 8 | 902 | (KAEMPFEROL) $C_{15}H_{10}O_6$, MW = 286 | 5 Glc<br>2 Rha | (4) |

FIG. 7

PROCEDURE FOR THE SIMULTANEOUS QUANTITATIVE AND QUALITATIVE ANALYSIS OF BOTH FLAVONOID GLYCOSIDES AND STEROIDAL GLYCOSIDES

FIELD OF THE INVENTION

The invention relates to methods for the rapid industrially advantageous analysis of flavonoid and steroidal glycosidic compounds in natural products. Existing methods of equivalent analytical power are cumbersome, time consuming and expensive as well as being difficult to implement in the context of the contract research laboratory. The analysis of flavonoid and steroidal glycosidic compounds in HOSTA leaves served as model system.

BACKGROUND OF THE INVENTION

Since ancient times a vast number of natural remedies of plant and animal origin has been used for medical treatment and disease prevention (Shibata, S., *The Chemistry of Chinese Drugs,* American Journal of Chinese Medicine (1979) 7(2): 103–141). The earliest known recorded recommendation of plants use to fight cancer appeared in the Ebers papyrus of Egypt dating from 1550 BC but this document implied an existence of already highly developed knowledge from far earlier times (Hartwell, J. L., et al., *Antineoplastic Principles in Plants: Recent Developments in the Field,* Advances in Pharmacology (1969) 1: 117–209). A fast growing body of evidence obtained in the recent years by utilization of modern scientific, experimental and clinical methods confirms the biological activity of many micro components of plants that can be utilized in prevention or treatment of a variety of chronic diseases, including cancer and cardiovascular disease (Rao, A. V., et al., *Anticarcinogenic Effects of Saponins and Phytosterols,* American Chemical Society Symposium Series (1997) 662: 313–324; Ghai, G., et al, U.S. Pat. No. 5,955,269; Hartwell, J. L., *Types of Anticancer Agents Isolated from Plants,* Cancer Treatment Reports (1979) 60(8): 1031–1067; Hutabarat, L. S., et al., *Development and Validation of an Isocratic High-performance Liquid Chromatographic Method for Quantitative Determination of Phytoestrogens in Soya Bean,* Journal of Chromatography A (1998) 795: 377–382).

Recently there has been visible a prominent trend to replace the conventional medicine approach, heavily dependent on the application of surgical intervention and use of potent synthetic drugs with many detrimental side effects (and thus being perceived by the public as inadequate or even harmful), by using herbal remedies or other forms of nutraceutical supplementation. Many herbal products available on the market are advertised as cures or preventative agents for a wide range of ailments. While a number of these claims might be true, based on their traditional use in folk medicine, for many of them there is little scientific basis underlying the claims of their health benefits.

Despite the fact that scientific evaluation of medicinal plants historically has been responsible for discovery of a multitude of modern medicine, approximately only 1% of plants has been analyzed so far.

When working with medicinal plants, the main goal is to isolate and identify the bioactive constituents. The typical strategy consists of the activity-guided fractionation of the plant extracts, leading to the isolation and identification of the active components. This approach is highly limited, time-consuming and may lead to easily missing any interesting lead compounds that don't poses the tested activity (Wolfender, J., et al., *Comparison of Liquid Chromatography/Electrospray, Atmospheric Pressure Chemical Ionization, Thermospray and Continuous-flow Fast Atom Bombardment Mass Spectrometry for the Determination of Secondary Metabolites in Crude Plant Extracts,* Journal of Mass Spectrometry and Rapid Communications in Mass Spectrometry (1995) (Special Issue): S35–S46).

The growing demand of the aging population for high quality herbal supplements offering scientifically confirmed health benefits and presented in a standardized form of known potency, purity and efficacy has created a conducive environment for facilitation of the basic research on the identification of new herbal medicines as well as requirement for development of time and cost effective, reliable quality control analytical testing procedures. The concern of healthcare government agencies for safe and efficacious herbal supplements has led to introduction of much more stringent legislation regulating the allowed medical claims and demanding from the industry presentation of analytical data proving the products purity, potency and efficacy. Thus both, the search for novel, scientifically evaluated herbal medicines and the screening, standardization and quality control of already known herbal remedies, either in the plant material or in different formulations (including extracts, tinctures, suspensions, capsules and compressed tablets) call for a development of a rapid and reliable analytical method.

The analysis of botanical material is not a trivial matter. Usually, a sample to be analyzed contains a very complex mixture of many components. Only some of them might be biologically active, while other may be toxic. Components of these complex mixtures are usually interacting amongst themselves and often work synergistically. Frequently, in many plants, dozens of species and strains of the same genus, differ substantially in content of the active ingredients. Even within the same plant, different parts often have different chemical composition. Furthermore, the presence and concentration of some substances depend greatly on the soil, location, season, time of harvest, storage conditions, handling methods, conditions and solvents used for extraction, etc. This diversity of important conditions affecting the quality of botanical remedies requires therefore implementation of stringent, well-designed and closely-monitored standard operating procedures of manufacturing to ensure consistency from batch to batch of a nutraceutical product, followed by application of an appropriate analysis to ensure consistent potency and efficacy.

The major aims of qualitative analyses in phytochemistry include monitoring of the preparative isolation and purification of phytochemicals, chemotaxonomic testing and drug identification and/or detection of adulterants (Maillard, M. P., et al., *Use of Liquid Chromatography-Thermospray Mass Spectrometry in Phytochemical Analysis of Crude Plant Extracts,* Journal of Chromatography (1993) 647: 147–154; Games, D. E., *Combined High Performance Liquid Chromatography Mass Spectrometry,* Biomedical Mass Spectrometry (1981) 8(9): 454–462).

Plant constituents often exist in the form of glycosides. These conjugates may or may not occur together with their respective aglycones. Many glycosides play an important role as drugs and dyes. Glycosides are thermally labile, polar and non-volatile compounds frequently differing in their solubility and biological activity from their respective aglycones. By changing a type and/or number of attached saccharides the physicochemical and biological properties of the glycosides can be modified (Vaccaro, W. D., et al., *Sugar-Substituted 2-Azetidinone Cholesterol Absorption*

*Inhibitors: Enhanced Potency by Modification of the Sugar,* Bioorganic & Medicinal Chemistry Letters (1998) 8: 313–318). Among phytochemicals existing in the glycosilated form that deserve a special attention due to their wide distribution in nature and a high number of beneficial biological and medicinal properties, are saponins and flavonoid glycosides.

Saponins are glycosides that commonly occur in higher plants where they are generally found in the roots, flowers and seeds. They are biosynthesized by more than 500 species belonging to almost 100 different families (Price, K. R., et al., *The Chemistry and Biological Significance of Saponins in Foods and Feedingstuffs,* Critical Reviews in Food Science and Nutrition (1987) 26(1): 27–135). They are also found in many marine organisms. Saponins belong to one of two groups depending on the structure of their aglycone moiety (sapogenin): the triterpine group, in which the aglycone is usually represented by oleanane, ursane or damarane skeleton, and the steroid group. The latter also includes the steroid alkaloids. The most common sugars encountered in saponins are hexoses (glucose, galactose and mannose), 6-deoxyhexoses (rhamnose), pentose (arabinose and xylose), uronic acids (glucuronic acid and galacturonic acid) or amino sugars (glucosamine and galactosamine) (Fang, S., et al., *Rapid Analysis of Steroidal Saponin Mixture Using Electrospray Ionization Mass Spectrometry Combined with Sequential Tandem Mass Spectrometry,* Rapid Communications In Mass Spectrometry (1998) 12: 589–594). Sugars may be linked to the sapogenin at one or two glycosylation sites (through an ether or/and an ester linkage), giving the corresponding monodesmodic or bidesmosidic saponins, respectively (Maillard, M. P., et al., *Determination of Saponins in Crude Plant Extracts by Liquid Chromatography-Thermospray Mass Spectrometry,* Journal of Chromatography (1993) 647: 137–146; Lee, M., et al., *Analysis of Saponins from Black Bean by Electrospray Ionization and Fast Atom Bombardment Tandem Mass Spectrometry,* Journal of Mass Spectrometry (1999) 34: 804–812).

Because of the glycosylation of their hydrophobic aglycones, saponins act as biological detergents and, when agitated with water, form a soapy lather that gives rise to name of this group of compounds. From a biological point of view saponins have diverse group properties, some deleterious, but many beneficial (Van Setten, D. C., et al., *Multiple-Stage Tandem Mass Spectrometry for Structural Characterization of Saponins,* Analytical Chemistry (1998) 70(20): 4401–4409). Some saponins have been used as plant drugs in folk medicine. They may exhibit cardiac activity, hemolytic activity, activity as fish poisons, hypocholesterolemic (Deninno, M. P., U.S. Pat. No. 5,698,526), immunostimulatory and anti-tumorigenic activity (Hostettmann, K., et al., *Saponins*—Chemistry and Pharmacology of Natural Product, Cambridge University, Cambridge (1995); Fuzzati, N., et al., *Identification of Soyasaponins by Liquid Chromatography—Thermospray Mass Spectrometry,* Journal of Chromatography A (1997)777: 233–238); Lee, M., et al., *Analysis of Saponins from Black Bean by Electrospray Ionization and Fast Atom Bombardment Tandem Mass Spectrometry,* Journal of Mass Spectrometry (1999) 34: 804–812). They can be used as bitterness and sweetness modifiers, allelochemicals and cosmetic ingredients. Saponins have a potential as pharmaceutical synthons (Mostad, H. B., et al., *Separation and Characterization of Oleanene-type Pentacyclic Triterpenes from Gypsophila Arrostii by Liquid Chromatography-Mass Spectrometry,* Journal of Chromatography (1987) 396: 157–168) and have been used in hormone synthesis (Hardman, R., Board of Pharmaceutical Sciences (editor), *Conception and Contraception,* Exerpta Medica, Amsterdam, (1975) p. 60).

The second important class of phytochemicals which attracted a high interest due to its wide distribution in nature and diversified biological properties are flavonoids. These polyphenolic compounds, apart from catechins and proanthocyanidins, consist mainly of glycosides of flavonols, flavons, flavanones, anthocyanins and less frequently isoflavons or free aglycones. Flavonoids play important role in the ecology of plants. Because of their attractive colors, flavonols, flavons, and anthocyanidins are likely to be a visual signal for pollinating insects. Catechins and other flavonols have astringent properties and they act as feeding repellants, while isoflavones are important plant-protective phytoalexins (Pietta, P., *Flavonoids in Medicinal Plants,* Antioxidant Health Dissertation (1998), 7 (Flavonoids in Health and Disease), 61–100). Flavonoids represent an important constituent of many edible plants and are present in foods and beverages derived from plants.

Some flavonoid-containing species have been used in traditional medicine. Recently these phytomedicines have been extensively investigated and their health benefits confirmed in many cases for the long-term treatment of mild and chronic diseases or in attaining and maintaining a condition of well-being, (Pietta, P. G, et al., *Fitomedicine e Nutrienti,* Verona: Ricchiuto G M, (*1996*)). Flavonoids function as strong antioxidants (Bors, W., et al., *Radical Chemistry of Flavonoid Antioxidants,* Antioxidants in Therapy and Preventative Medicine (1990) 264: 165–170; Budzianowski, J., et al., *Studies on Antioxidative Activity of Some C-Glycosylflavones,* Polish Journal of Pharmacology and Pharmacy (1991) 43: 395–401), free-radical scavengers (Lonchampt, M. et al., *Protective Effect of a Purified Flavonoid Fraction against Reactive Oxygen Radicals,* Arzneimittelforschung (1989) 39(8): 882–885), and metal chelators and their biological properties can also be linked with their interaction with enzymes, adenosine receptors, and biomembranes (Saija, A., et al., *Flavonoids as Antioxidant Agents: Importance of their Interaction with Biomembranes,* Free Radical Biology & Medicine (1995) 19(4): 481–486). Many of the bioflavonoids exhibit very beneficial pharmacological activities, such as anti-inflammatory, antiallergic, antimicrobial, antioxidative, enzyme-inhibitory effects, etc. (Von Wacker, A., *Antivirale Wirkung von Pflanzeninhaltsstoffen,* Arzneimittelforschung (1978) 28(3): 347–350; Frazier, S. E., U.S. Pat. No. 4,238,483; Havstee, B., Biochemical Pharmacology (1983) 32: 1141; Pathak,D., et al., Fitoterapia (1991) 62:371).

The identification of individual flavonoids, sapogenins and their glycosides has long been carried out by Mass Spectrometry (Dawidar, A. M., et al., *Mass Spectra of Steroid Saponins,* Journal of Pharmaceutical Sciences (1974) 63: 140–142; Harborn and Williams. The Flavonoids. Ed, Harborn, J. B. et al., Chapman and Hall, (1975): 376–441; Franski, R., et al., *Application of Mass Spectrometry to Structural Identification of Flavonoid Monoglycosides Isolated from Shoot of Lupin (Lupinus Luteus L.),* Acta Biochimica Polonica (1999) 46(2): 459–478) and Ultraviolet Spectroscopy (Nakaori, T., et al, Journal of Pharmaceutical Sciences Japan. (1956) 76: 323; Lunte, S. M., *Structural Classification of Flavonoids in Beverages by Liquid Chromatography With Ultraviolet-visible and Electrochemical Detection,* Journal of Chromatography (1987) 384: 371–382; Tsuchiya, H., *High-Performance Liquid Chromatographic Analysis of Polyhydroxyflavones using Solid-Phase Borate-Complex Extraction,* Journal of Chromatography B (1998) 720: 225–230). More recently 13C-NMR has been used for the structural elucidation of flavonoid glycosides Guinaudeau, H., et al., Phytochemistry (1981) 20: 1113; Hosny, M., *Novel Isoflavone, Cinnamic Acid, and Triterpenoid Glycosides in Soybean Molasses,* Journal of Natural Products (1999) 62(6): 853–858). These techniques were executed on highly purified compounds and were not applied to mixtures.

Separation of individual flavonoids, sapogenins and their glycosides from each other has long been carried out by Paper, Thin Layer and Open Column Chromatography (Harborn, J. B., et al, *Flavone and Flavonol Glycosides. Flavonoids: Advances in Research* (1982) 261–311. Editor: Harborne, J., Wolf, W. J., et al, Journal of American Oil Chemists Society. (1970) 47: 89).

More recently HPLC has been used for the separation of individual flavonoids, sapogenins and their glycosides from each other (Stewart et al., *Biochemical Systems Ecology,* (1980) 8: 119; Galensa, R., et al, *Analyse von Flavonoidglycosiden durch Hochdruck-Flusskeits-Chromatographie,* (1978) 166: 355–358; Domon, B., Journal of Chromatography (1984) 315: 441). These techniques gave limited resolution between individual glycosides of either the flavonoids or the sapogenins. Selectivity between the flavonoid and sapogenin classes of compounds was effected through chemical purification steps or separate preparative chromatographic steps.

The combination of HPLC and Diode Array UV-Visible Detection gave new possibilities in qualitative analysis of flavonoids in plant extracts (Hasler, A., et al., *High-performance Liquid Chromatographic Determination of Five Widespread Flavonoid Aglycones,* Journal of Chromatography (*1990*) 508: 236–240; Inada, S., et al., U.S. Pat. No. 4,968,787 and 39$^{th}$ Annual Congress on Medicinal Plant Research September 1991). Information about the type and number of glycosidic units was lost due to the preparation. The extraction and purification did not address the identification and quantization of individual glycosides. Mass Spectrometry with Thermospray Ionization permitted routine online analysis of a number of glycosides of both flavonoid and sapogenin classes, but sensitivity was limited and interpretation was complicated by the frequent formation of artifacts (Iida, J., et al., *Application of Thermospray Liquid Chromatography/Mass Spectrometry to Analysis of Glycosides,* Analytical Sciences (1991) (Supplement): 963–966; Maillard, M. P., et al., *Thermospray LC-MS Analysis of Saponins in Crude Plant Extracts,* Planta Medica (1992) 58(Supplement Issue 1): A 673; Wolfender, J. L., et al., Liquid Chromatographic-Thermospray Mass Spectrometric Analysis of Crude Plant Extracts Containing Phenolic and Terpene Glycosides, Journal of Chromatography (1993) 647: 183–190; Wolfender, J., et al., *Comparison of Liquid Chromatography/Electrospray, Atmospheric Pressure Chemical Ionization, Thermospray and Continuous-flow Fast Atom Bombardment Mass Spectrometry for the Determination of Secondary Metabolites in Crude Plant Extracts,* Journal of Mass Spectrometry and Rapid Communications in Mass Spectrometry (1995) (Special Issue): S35–S46; Pietta, P., et al., *Thermospray Liquid Chromatography-Mass Spectrometry of Flavonol Glycosides From Medicinal Plants,* Journal of Chromatography A (1994) 661: 121–126). Moreover, due to the relatively energetic ionization of the thermospray technique the higher glycosides were not observed. Few such compounds above 850 Da were reported with this technique. Continuous Flow Fast Atom Bombardment gave some advantages in ionization of small polar molecules but at the cost of instrumental complexity and reliability (Wolfender, J., et al., *Comparison of Liquid Chromatography/Electrospray, Atmospheric Pressure Chemical Ionization, Thermospray and Continuous-flow Fast Atom Bombardment Mass Spectrometry for the Determination of Secondary Metabolites in Crude Plant Extracts,* Journal of Mass Spectrometry and Rapid Communications in Mass Spectrometry (1995) (Special Issue): S35–S46; Wolfender, J. L., et al., *Liquid Chromatography Combined with Thermospray and Continuous-flow Fast Atom Bombardment Mass Spectrometry of Glycosides in Crude Plant Extracts,* Journal of Chromatography A (1995) 712: 155–168).

The advent of Electrospray Ionization permitted molecules to be ionized with very low energies under atmospheric pressures and at room temperatures. Very polar, high molecular weight species could be routinely analyzed with little artifact formation that could complicate interpretation (Hakkinen, S., et al., *High-performance Liquid Chromatography with Electrospray Ionization Mass Spectrometry and Diode Array Ultraviolet Detection in the Identification of Flavonol Aglycones and Glycosides in Berries,* Journal of Chromatography A (1998) 829: 91–100; Schopke, T., et al., *Application of MS-MS for the Rapid, Comparative Analysis of Saponin Mixtures as Exemplified by the Deacylated and Partially Deacylated Triterpenoid Saponins of Bellis Annua,* Planta Medica (1996) 62: 336–340; Mauri, P. L., et al., *Liquid Chromatography/Electrospray Ionization Mass Spectrometric Characterization of Flavonol Glycosides in Tomato Extracts and Human Plasma,* Rapid Communications in Mass Spectrometry (1999) 13: 924–931; Stobiecki, M., et al., *Detection of Isoflavonoids and their Glycosides by Liquid Chromatography/Electrospray Ionization Mass Spectrometry in Root Extracts of Lupin (Lupinus Albus),* Pytochemical Analysis (1999) 10: 198–207). The technique also permits the use of Collision Induced Fragmentation for generating ions that aids in structure elucidation. Gelpi, E., *Biomedical and Biochemical Applications of Liquid Chromatography-Mass Spectrometry,* Journal of Chromatography A (1995) 703:59–80. Negative ion mode in Electrospray Ionization was also shown to have advantages (Wolfender, J., et al., *Comparison of Liquid Chromatography/Electrospray, Atmospheric Pressure Chemical Ionization, Thermospray and Continuous-flow Fast Atom Bombardment Mass Spectrometry for the Determination of Secondary Metabolites in Crude Plant Extracts,* Journal of Mass Spectrometry and Rapid Communications in Mass Spectrometry (1995) (Special Issue): S35–S46; Watson, D. G., et al., *Analysis of Flavonoids in Tablets and Urine by Gas Chromatography/Mass Spectrometry and Liquid Chromatography/Mass Spectrometry,* Rapid Communications in Mass Spectrometry (1998) 12: 153–156).

The combination of three powerful techniques LC/DAD/ESIMS was used to study the aglycones and glycosides present in berries (Hakkinen, S., et al., *High-performance Liquid Chromatography With Electrospray Ionization Mass Spectrometry and Diode Array Ultraviolet Detection in the Identification of Flavonol Aglycones and Glycosides in Berries,* Journal of Chromatography A (1998) 829: 91–100; Justesen, U., et al., *Quantitative Analysis of Flavonols. Flavones, and Flavanones in Fruits, Vegetables and Beverages by High-performance Liquid Chromatography with Photo-diode array and Mass Spectrometric Detection,* Journal of Chromatography (1998) 799: 101–110). These works however largely concentrated on the identification of the flavonoid aglycones or of glycosides of no greater than two units.

The present invention provides a fast and reliable method for the simultaneous analysis of both flavonoid glycosides and steroidal glycosides in one procedure. As a model to show the usefulness of this technique we have chosen plants from Hosta genus which belongs to the subfamily Asphodeloideae in Liliaceae. These plants are widely distributed thus offering easy and economical access to this source of flavonoid and steroidal glycosides of potential medicinal application. The young leaves and buds of the plants are edible and the leaves and rhizomata have been used as a folk medicine in China and Japan (Jiang Su New Medical College (ed.), "*Dictionary of Traditional Chinese Crude Drugs*", vol.1, Shanghai Scientific Technologic Publishers, Shanghai, (1977), p.557). A steroidal saponin identified as hexasaccharide and prepared from the extract of dried Hosta leaves by O. Masamitsu, et al. (Ochi, M., et al., *Steroid Saponin from Hosta and Antimicrobial and Antitumor Agents Containing It*, JP 10 114,791 [98 114,791] (C1. C07J71/00), May 6, 1998, Appl. 96/270,292, Oct. 11, 1996; 12 pp; CA 129: 32293w; Ochi, M., et al., *Novel Steroidal Saponin and Antimicrobial Agents and Antitumor Agents Containing It*, JP 10 158,295 [98 158,295] (C1. C07J71), Jun. 16, 1998, Appl. 96/320,142, Nov. 29, 1996; 12 pp; CA 129:113511t) exhibit antibacterial and antitumor activity while some of the steroidal glycosides identified by M. Mimaki group displayed cytostatic activity on HL-60 cells.

Although eight kaempferol glycosides (Budzianowski, J., *Kaempferol Glycosides from Hosta Ventricosa*, Phytochemistry (1990) 29(1): 3463–3467) and twenty six steroidal glycosides (Takeda, K., et al., *Studies on the Steroidal Components of Domestic Plants—XLVI Constituents of Hosta Species (3) Δ25(27)-Sapogenins,* Tetrahedron, (1965) 21: 2089–2093; Takeda, K., et al., *Studies on Biochemical Transformation of Plant Steroids, Part Biochemical Interconversion of the Δ25(27)-and the Saturated 25D- or 25L-Sapogenins,* Journal of Chemical Society C (1967) (9): 876–882; Takeda, K., et al., *Studies on Biochemical Transformation of Plant Steroids,* Part II. *Biochemical Conversion of Gitogen into 12-Oxygenated Sapogenins in Hosta Kiyosumiensis,* Chemical and Pharmaceutical Bulletin (1968) 16(2): 275–279; Mimaki, Y., et al., *Steroidal Saponins from the Underground Parts of Hosta Longpipes and Their Inhibitory Activity on Tumor Promoter-Induced Phospholipid Metabolism,* Chemical and Pharmaceutical Bulletin (1995) 43(7): 1190–1196; Mimaki, Y., et al., *Steroidal Saponins from Hosta Longpipes and Their Inhibitory Activity on Tumor Promoter-Induced Phospholipid Metabolism of HeLa Cells,* Phytochemistry (1996) 42(4): 1065–1070; Mimaki, Y., et al., *Steroidal Glycosides from the Underground Parts of Hosta Plantaginea Var. Japonica and Their Cytostatic Activity on Leukemia HL-60 Cells,* Phytochemistry (1997) 44(2): 305–310; Ochi, M., et al., *Steroid Saponin from Hosta and Antimicrobial and Antitumor Agents Containing It,* JP 10 114,791 [98 114,791] (C1. C07J71/00), May 6, 1998, Appl. 96/270,292, Oct. 11, 1996; 12 pp; CA 129: 32293w; Mimaki, Y., et al., *Steroidal Saponins from the Rhizomes of Hosta Sieboldii and Their Cytostatic Activity On HL-60 Cells,* Phytochemistry (1998) 48(8): 1361–1369) have been previously separated from Hosta leaves and Hosta rhizomers, respectively, there has been no reports of any comprehensive procedure to extract simultaneously both classes of glycosides from the Hosta leaves.

The eight reported kaempferol glycosides after separation were analyzed and identified individually by TLC, and UV, $^1$H and $^{13}$C NMR spectroscopies.

Similarly, the previously reported steroidal glycosides extracted from Hosta root after separation and purification were analyzed and identified individually by NMR, IR and in some cases by negative-ion FAB-MS spectrometry.

SUMMARY OF THE INVENTION

The present invention provides a method for the simultaneous analysis of both flavonoid glycosides and steroidal glycosides in one procedure. Compounds glycosidic units from 0 to 4 or more can be readily identified for both compound classes. In the preferred embodiment the method is comprised of an extraction and a pre-purification step followed by an instrumental technique (LC/DAD/ESI/MS) that allows for accurate qualitative and quantitative measurements. In another embodiment the pre-purification step is eliminated from the procedure. The resulting method is useful for screening functions and gives detailed data in the shortest amount of time.

BRIEF DESCRIPTION OF THE DRAWINGS

FIG. 4 is a graph depicting chemical structures of eight kaempferol glycosides, previously found in the extract of Hosta leaves.

FIG. 7 is a table containing a list of eight new glycosidic compounds identified for the first time in the Hosta leaves extracts by application of the presented procedure.

DETAILED DESCRIPTION OF THE PREFERRED EMBODIMENT

Figure 1:
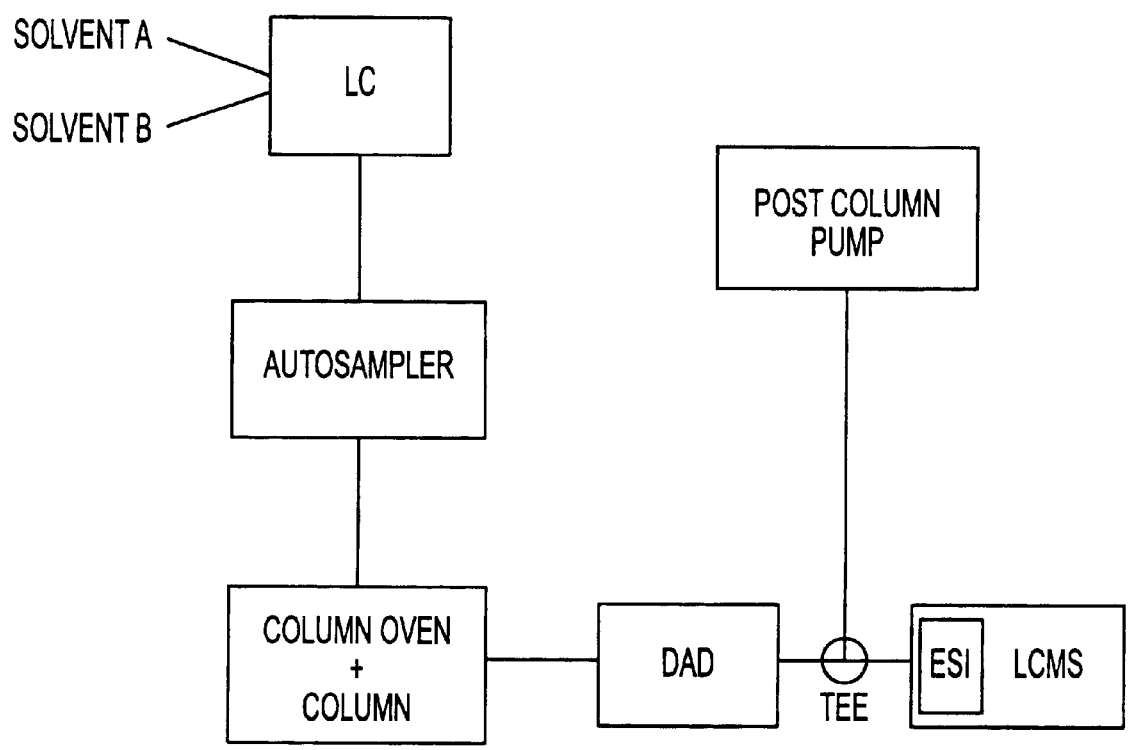
FIG. 1 is a graph illustrating details of the instrumental setup.

The present invention is applicable, but not limited, to the extraction, isolation and simultaneous determination of both flavonoiod and steroidal glycosides from plants, fresh or dried, and other potential natural sources of nutraceuticals. Other classes of phytochemicals can also be subjected to the claimed procedure. This procedure is also fully applicable to qualitative and quantitative analysis of different forms of herbal supplementations, such as powders, tinctures, suspensions, solutions, syrups, capsules, tablets, etc.

The biological material, such as plant, should be collected and stored under properly designed and controlled conditions, to ensure the consistency in the content of active components. Measures should be applied to avoid the presence of any harmful contaminants, such as pesticides, herbicides, heavy metals, etc.

If drying is recommended, the chemical and enzymatic sensitivity of the active components should be considered. Thus the avoidance of exposure to light, elevated temperatures, oxygen presence or prolonged storage in aqueous solution prone to facilitate biochemical degradation should be considered and applied, if necessary.

Prior to the extraction procedure sample should be prepared by chopping into small pieces, blending, grounding or crushing, in order to improve the contact of solvent with the extracted matter.

In the present invention, for analytical purposes, the extraction of the polar phytochemicals such as bioflavonoids or saponins from the plant or marine matter or their formulations is achieved by the application of water or aqueous solutions of a variety of polar solvents such as lower alcohols, ketones, or acetonitrile. The elevated temperature and repeated extraction procedures might be used to improve the extraction effectiveness. The effectiveness can be further enhanced by stirring, shaking or sonication.

Plant or marine matter consist of a multitude of components, both polar and non-polar. In order to provide a simple, sensitive and reliable method for analyzing for phytochemicals, such as flavonoid and steroidal glycosides, the sample should be treated to remove contaminants and other undesired components that would interfere with the analysis. Such a removal, for analytical purposes, can be achieved by precipitation of some undesired compounds by means of concentration of the extract volume and/or refrigeration.

Further removal of interfering less polar compounds can be achieved by subjecting the crude extract to liquid-liquid extraction with a water immiscible organic solvent, such as alkanes, cycloalkanes, ethers or lower esters.

The purification of sample from polar components such as inorganic salts, simple sugars, and aminoacids that could interfere with the final analysis of the phytochemicals of interest can be achieved, for analytical purposes, by application of open column or flash column chromatography using a variety of different stationary phases, such as polyamide resin or a weakly acidic cation exchange resin, such as Amberlite IRC-50, and mixture of water and lower alcohols as mobile phase.

Such separation can be easily monitored by HPLC or TLC with a variety of detection methods. The column chromatography may also utilize other modes, such as normal phase chromatography with application of silica gel or alumina or gel filtration approach.

Thus such extracted and pre-purified sample can be then subjected to qualitative and quantitative analysis by the application of reverse phase HPLC in an isocratic or preferably gradient mode. The combined application of two independent and powerful detection techniques of Electrospray Mass Spectrometry and Diode Array Spectroscopy allow for the selective and simultaneous identification of the individual components, such as phytochemicals of interest, contained in the pre-purified extract. The application of Electrospray Mass Spectrometry detection for the thermally liable compounds prevents creation of artifacts that may lead to misinterpretation of the instrumental data that was frequently possible with the previously used ionization techniques. It was found that the application of negative ion mode yields patterns that are more informative than other techniques, decreasing at the same time the risk of the artifact formation and data misinterpretation. Furthermore, the post-column application of triethylamine enhances the sensitivity of this method of detection. FIG. 1 details the instrumental setup.

The sample preparation combined with the applied detection system presented in this invention yield sensitive and extensive qualitative information about the individual components of the analyzed extract, such as, for example flavonoid and steroidal glycosides. This information includes, but is not limited, to molecular weight, number and type of glycoside substituents, and from the Diode Array Spectroscopy absorption patterns, this technique allows for differentiation amongst different types of aglycones present in the components of the extract.

Figure 2:
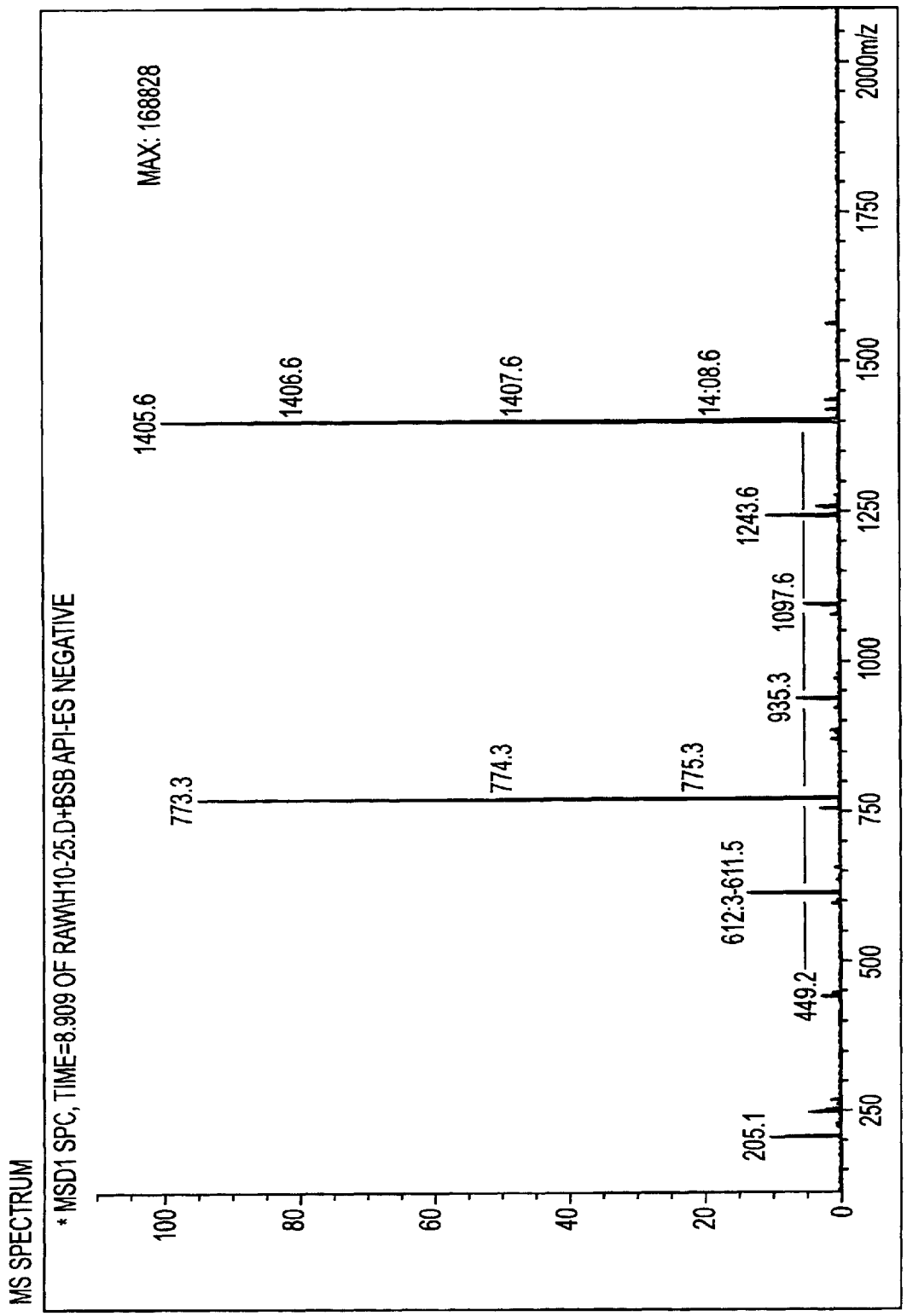
FIG. 2 is a graph showing an application of Collisionally Induced Dissociation for the identification of sugars from a steroidal hexaglycoside where the steroidal aglycone corresponds to an open spiro ring sapogenin i.e. (Gitogenin+$H_2O$) and the losses of m/e 162 fragment indicates the presence of five hexose (most likely glucose) moieties and the loss of m/e 146 fragment indicates the presence of one 6-deoxyhexose (most likely α-L-rhamnose).
Figure 3:
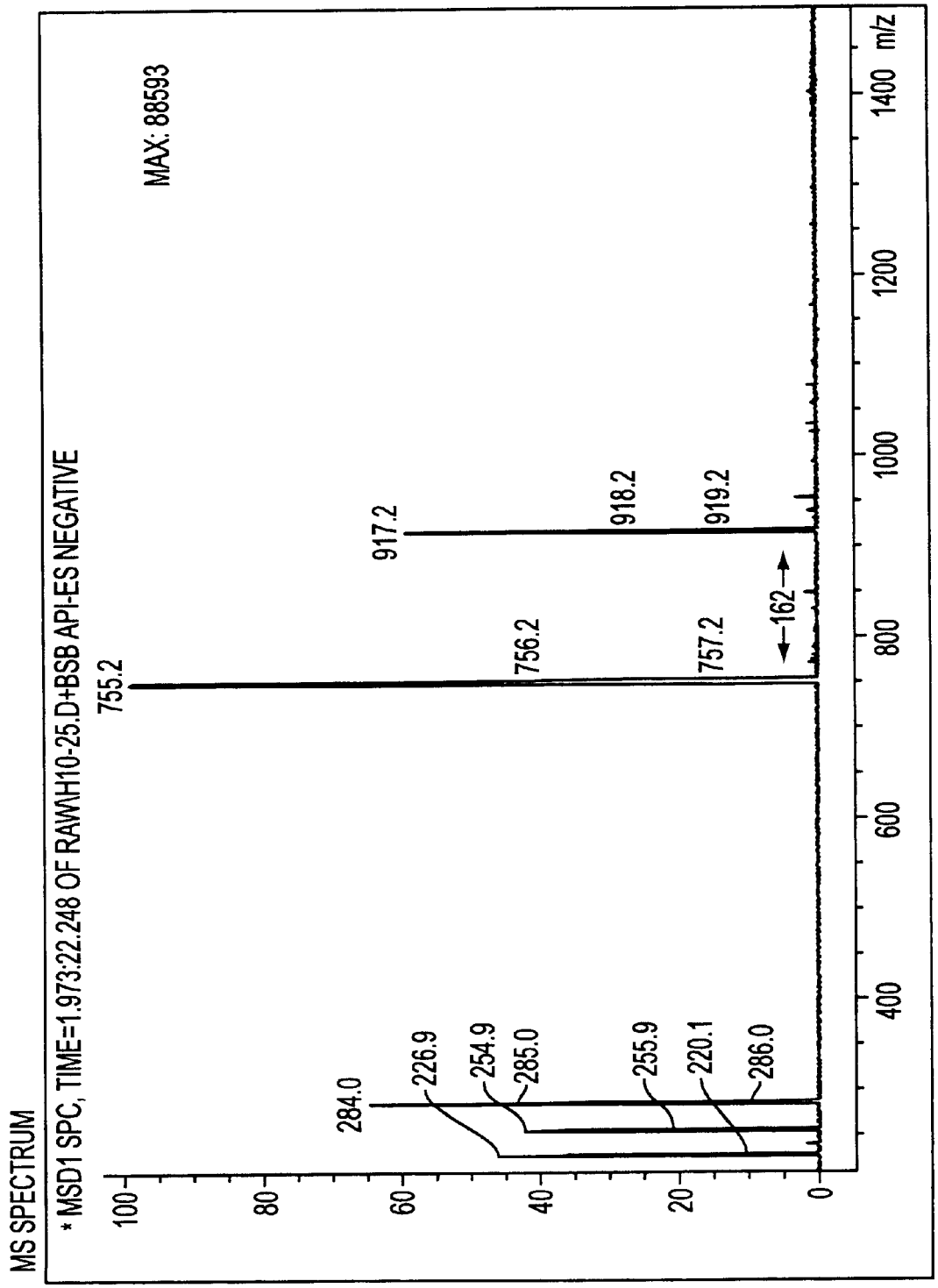
FIG. 3 is a graph showing an application of Collisionally Induced Dissociation for the identification of sugars from a flavonoid tetraglycoside where the flavonoid aglycone corresponds to kaempferol and the loss of m/e 162 fragment indicates the presence of hexose (most likely glucose).

The application of the presented procedure in combination with the use of Collisionally Induced Dissociation can produce mass spectral patterns that can allow structural data to be deduced. Those skilled in the art will recognize that m/e 162 fragment could be related to a loss of hexose (e.g. glucose), that of m/e 146 fragment from the loss of 6-deoxyhexoses (e.g. rhamnose), and that of m/e 132 fragment from the loss of pentose (e.g. xylose) (see FIG. 2 and FIG. 3).

Figure 5:
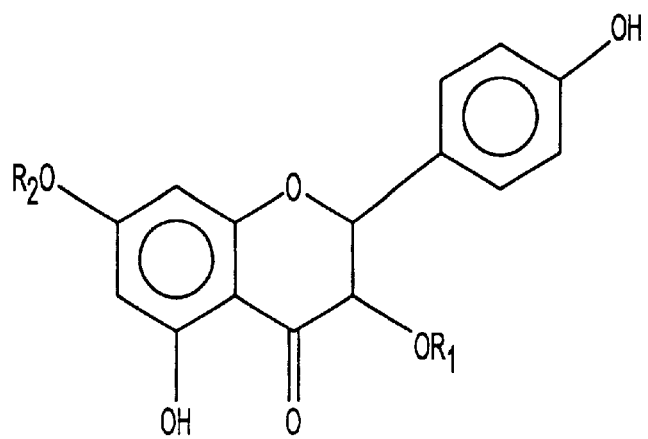
FIG. 5 is a graph depicting chemical structures of four steroidal glycosides, previously found in the extract of Hosta rhizomers.
Figure 6:
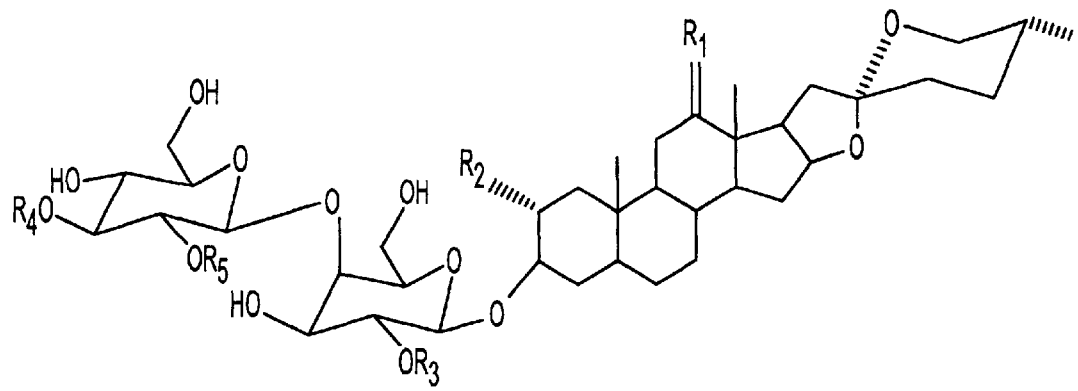
FIG. 6 is a table containing a list of all flavonoid and steroidal glycosides from the Hosta leaves extracts found by the application of this invention, and compared with glycosides previously identified in the literature.

As a very educational and powerful example for the application of this invention can serve the application of the present procedure for the extraction, purification and analysis of flavonoid and steroidal glycosides from Hosta leaves. Thus this invention has allowed for the first time simultaneously identify a total of twenty glycosides, both from the flavonoid and steroidal class (Table 1, FIG. 4). Among the identified glycosidic compounds were all eight kaempferol glycosides, previously reported by J. Budzianowski (structures of which are shown in FIG. 5), and 4 steroidal glycosides, previously reported in the literature by the Japanese researchers for the extracts of Hosta rhizomers (structures of which are shown in FIG. 6). This procedure, with application of Collisionaly Induced Dissociation also allowed for the identification of eight new, previously not detected in the Hosta plant extracts glycosidic compounds, seven of which were identified as steroidal tetra, penta, and hexaglycosides, and one as kaempferol tetraglycoside (Table 2, FIG. 7).

The application of the presented method of extraction, purification and separation can be easily adopted to a preparation of pre-purified and standardized mixtures of phytochemicals or the individual compounds in a pure form for additional structural elucidation and/or conformation (e.g., by means of NMR spectroscopy or X-ray analysis) as well as for their screening for biological activity.

The presented invention does not require any additional steps, such as chemical derivation. However, it can be combined with either an analysis of partly and/or fully hydrolyzed material, as well as consecutive derivation of glycosides, and subjecting these samples to further HPLC/MSD/DAD or other methods of analysis.

Applications of appropriate standards allow for an easy, sensitive and highly reliable method of quantitative analysis, and therefore, can be widely utilized for standardization of nutraceuticals.

Thus the presented procedure represents a much more industrially advantageous method for the execution of these analyses, particularly in the field of research, standardization and quality control of herbal and marine matter, or any of their nutraceutical supplement formulations.

EXAMPLE 1

Figure 8:
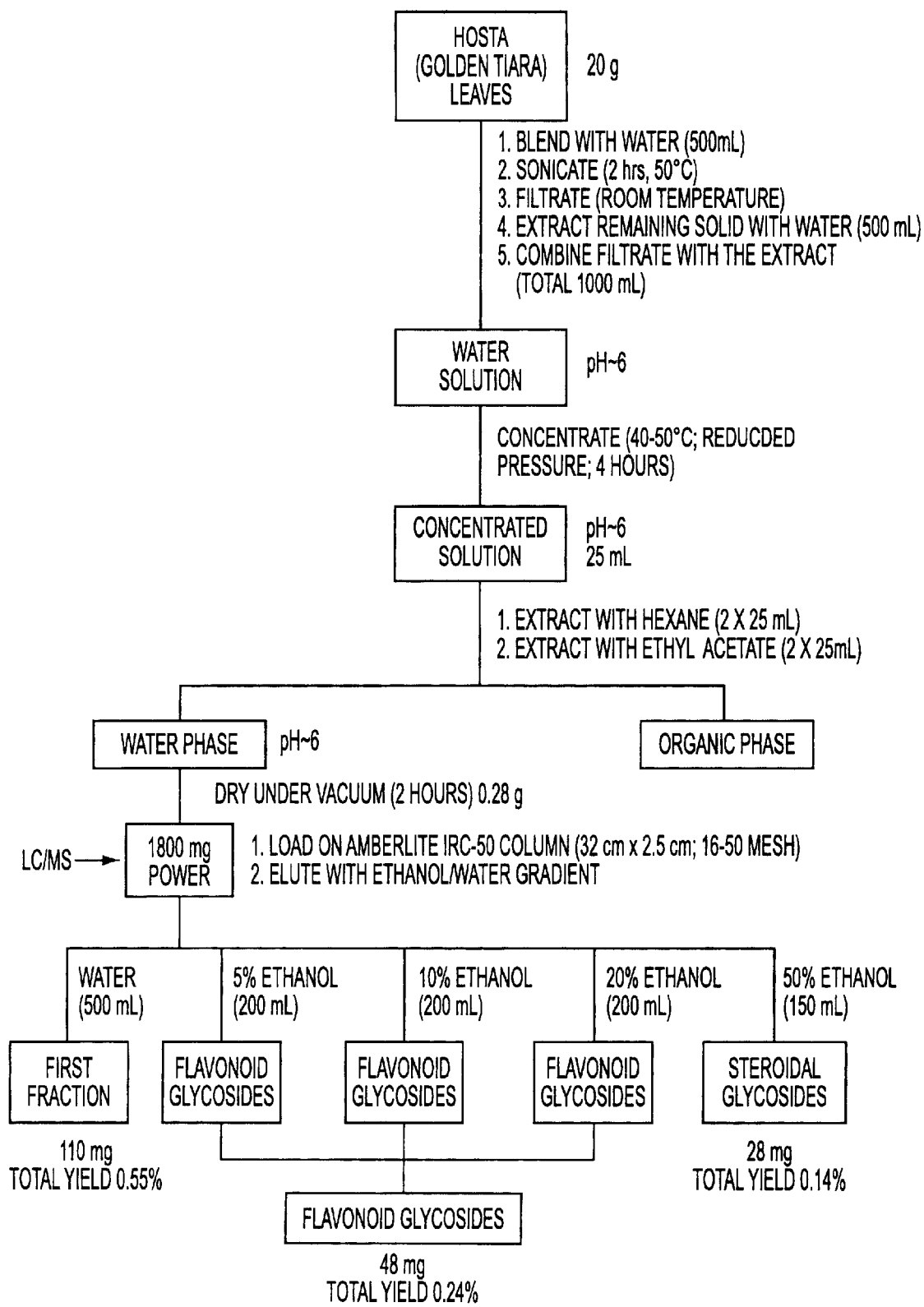
FIG. 8 is a graph that summarizes the procedure used for extraction, pre-purification and analyses of Hosta leaves in Example 1.

The procedure for extraction, pre-purification and analysis of Hosta leaves is depicted in FIG. 8. The fresh Hosta leaves (Golden Tiara) were hand picked in October. Fresh leaves (20 g) were chopped into small pieces and then ground in a blender with water (500 mL), followed by sonication for 2 hours at 50° C. The extract was filtrated to separate and remove fibrous material. The extraction of the separated solid material was then repeated with another portion of water (500 mL). Both extracts were combined and concentrated to ca. 25 mL under reduced pressure on a Rotovapor. The concentrated aqueous solution was extracted twice with hexane (25 mL) followed by two-time extraction with ethyl acetate (25 mL). The aqueous phase was evaporated under vacuum to dryness to afford 0.28 g (1.4% yield) of the raw extract of flavonoid and steroidal glycosides in the form of powder. This powder (0.28 g) was dissolved in 3.0 mL of a mixture of water and ethanol (1:1) and subjected to HPLC/MS analysis.

The solution of this raw extract was separated by a column chromatography on Amberlite IRC-50 resin (16–50 mesh, Sigma Company) with gradient elution of increasingly higher content of ethanol in water. The chromatography was monitored by HPLC/MSD/DAD. The first fraction eluted with water (500 mL) contained mainly some polar interfering compounds, such as sugars; the evaporation under vacuum to dryness yielded a solid powder (110 mg). The second fraction was eluted with 5% ethanol-water solution (200 mL). The third fraction was eluted with 10% ethanol-water solution (200 mL) and the fourth fraction eluted with 20% ethanol-water solution (200 mL). The second, third and fourth fractions were combined and evaporated under vacuum to dryness to afford 48 mg (0.24% yield) of a crude mixture of flavonoid glycosides. The fifth fraction was eluted with 50% ethanol-water solution (200 mL). This fraction was evaporated separately under vacuum to dryness to afford 28 mg (0.14% yield) of a crude mixture of steroidal glycosides.

The HPLC/MSD/DAD analysis was performed with a system that consisted of an HPLC 1100 series LC/MSD (Hewlett-Packard) instrument, autoinjector, quaternary pump with on-line vacuum degassing unit, thermostated column compartment and diode array detector. At the same time, a mass detector was used. The API-EI mode was chosen. The negative ion mode provided better sensitivity and the interpretation of the spectra was found to be easier. So the analysis results were obtained in negative mode at fragmentation potential of 100 eV. A standard Zorbax C8 column (150 mm long×2.1 mm I.D.) with 5 μm particle size was used in these examples.

Operation conditions for the analysis were as follows:
Temperature 30° C.
Mobile phase consisted of an ACN/water mixture gradient:
  0–6 minutes ACN 15%
  6–18 minutes ACN from 15% to 90%
  18–20 minutes ACN from 90% to 15%
The mobile phase flow rate was 0.4 mL/min.
Wavelength of UV detector was recorded on 280 nm.
The mass ion scan was from 100 to 1800.

Figure 9:
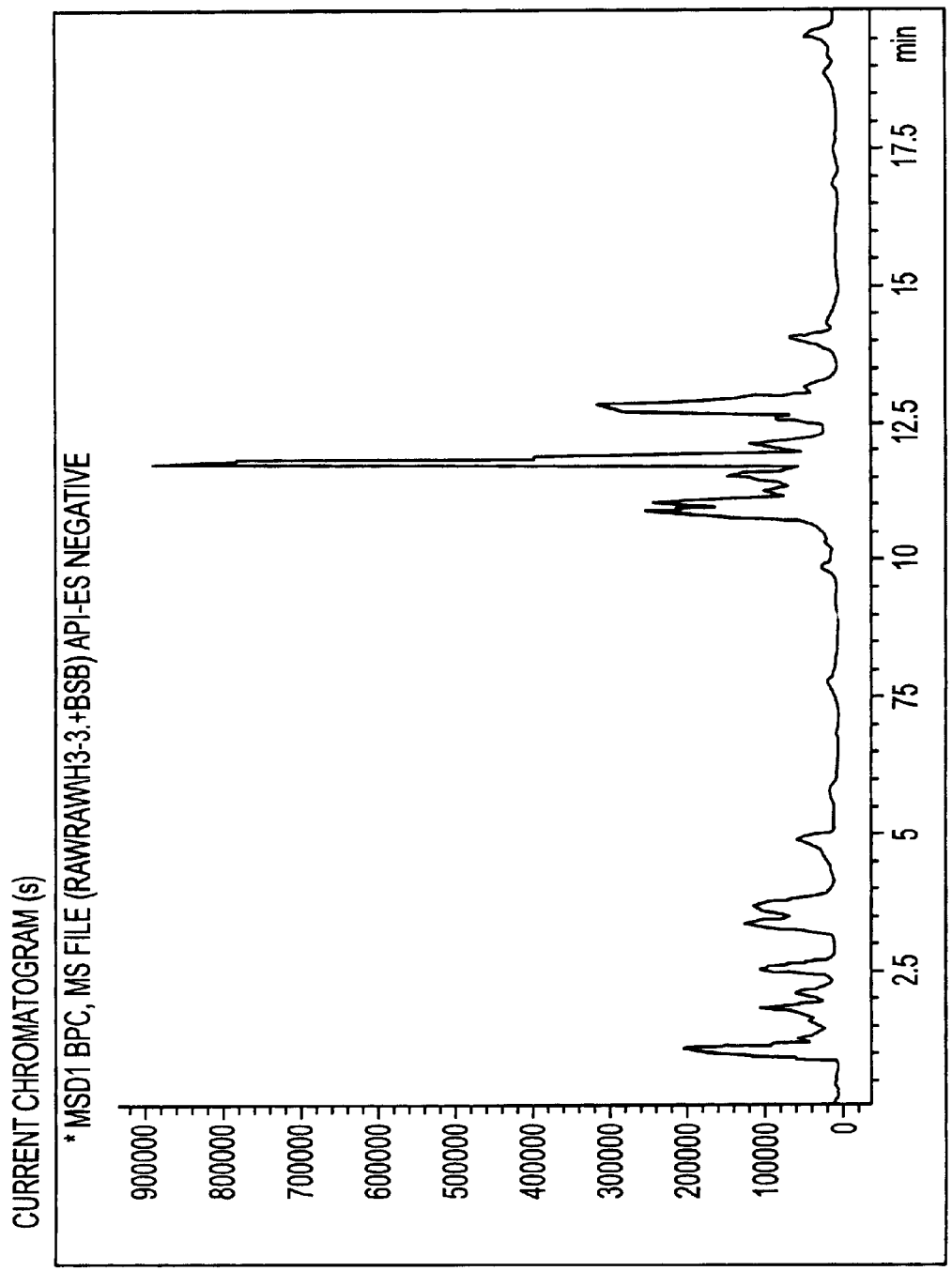
FIG. 9 is a LC/MS chromatogram of the raw extract from Example 1.

The recorded LC/MS chromatogram of the raw extract is presented in FIG. 9.

EXAMPLE 2

Figure 10:
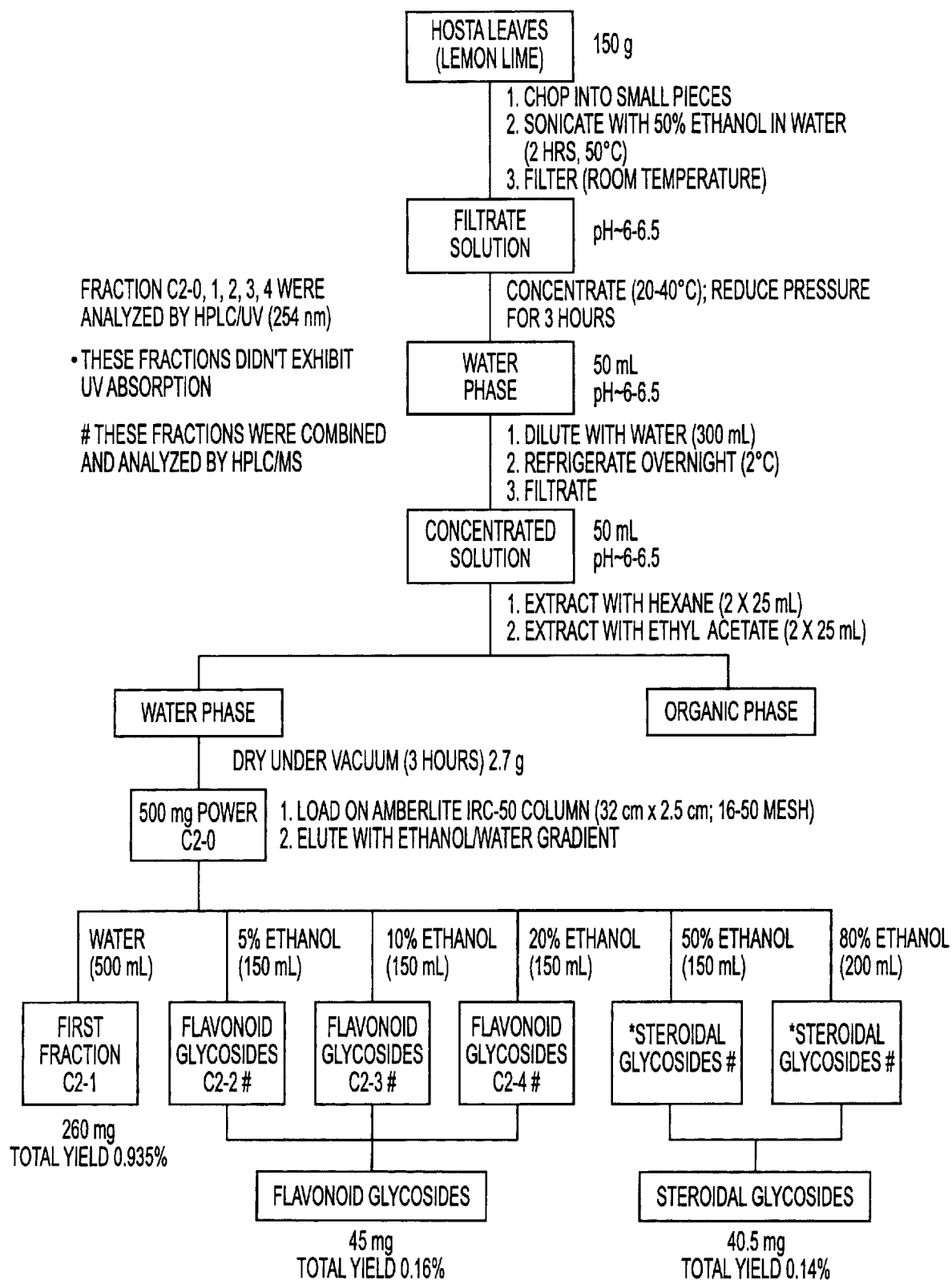
FIG. 10 is a graph that summarizes the procedure used for extraction, pre-purification and analyses of Hosta leaves in Example 2.

The procedure for extraction, pre-purification and analysis of Hosta leaves is depicted in FIG. 10. The fresh Hosta leaves (Lemon Lime) were hand picked in September. Fresh leaves (150 g) were chopped into small pieces and then ground in a blender with 50% aqueous ethanol solution (500 mL), followed by sonication for 2 hours at 50° C. The extract was filtrated to separate and remove fibrous material. The extract was concentrated to ca. 50 mL under reduced pressure on a Rotovapor. The concentrated aqueous solution was diluted to 300 mL with water, refrigerated overnight and the formed precipitate of undesired components such as alkylphenols and fat was filtered out. The resulted filtrate was extracted twice with hexane (25 mL) followed by two time extraction with ethyl acetate (25 mL). The aqueous phase was evaporated under vacuum to dryness to afford 2.7 g (1.8% yield) of the raw extract of flavonoid and steroidal glycosides in the form of powder. This powder (0.5 g) was dissolved in 5.0 mL of a mixture of water and ethanol (1:1) and subjected to chromatographic separation. The separation was performed by a column chromatography on Amberlite IRC-50 resin (16–50 mesh, Sigma Company) with gradient elution of increasingly higher content of ethanol in water. The chromatography was monitored by HPLC/UV and the analysis of the final combined fractions by HPLC/MSD/DAD. The first fraction eluted with water (500 mL) contained mainly some polar interfering compounds, such as sugars; the evaporation under vacuum to dryness yielded a solid powder (260 mg). The second fraction was eluted with 5% ethanol-water solution (150 mL). The third fraction was eluted with 10% ethanol-water solution (150 mL) and the fourth fraction eluted with 20% ethanol-water solution (150 mL). The second, third and fourth fractions were combined and evaporated under vacuum to dryness to afford 45 mg (0.16% yield) of a crude mixture of flavonoid glycosides. The fifth fraction was eluted with 50% ethanol-water solution (150 mL) and the sixth one with 80% ethanol-water solution (200 mL). Fractions five and six were combined and evaporated separately under vacuum to dryness to afford 40.5 mg (0.145% yield) of a crude mixture of steroidal glycosides.

The HPLC/MSD/DAD analysis was performed with a system that consisted of an HPLC 1100 series LC/MSD (Hewlett-Packard) instrument, autoinjector, quaternary pump with on-line vacuum degassing unit, thermostated column compartment and diode array detector. At the same time, a mass detector was used. The API-I mode was chosen. The negative ion mode provided better sensitivity and the interpretation of the spectra was found to be easier. So the analysis results were obtained in negative mode at fragmentation potential of 400 eV. A standard Zorbax C8 column (150 mm long×2.1 mm I.D.) with 5 μm particle size was used in these examples.

Operation conditions for the analysis were as follows:
Temperature 30° C.
Mobile phase consisted of an ACN/water mixture gradient:
  0–15 minutes ACN 15%
  15–20 minutes ACN from 15% to 90%
  20–25 minutes ACN 90%
  25–30 minutes ACN from 90% to 15%
The mobile phase flow rate was 0.4 mL/min.
Wavelength of UV detector was recorded on 280 nm.

The mass ion scan was from 100 to 1800.

Figure 11:
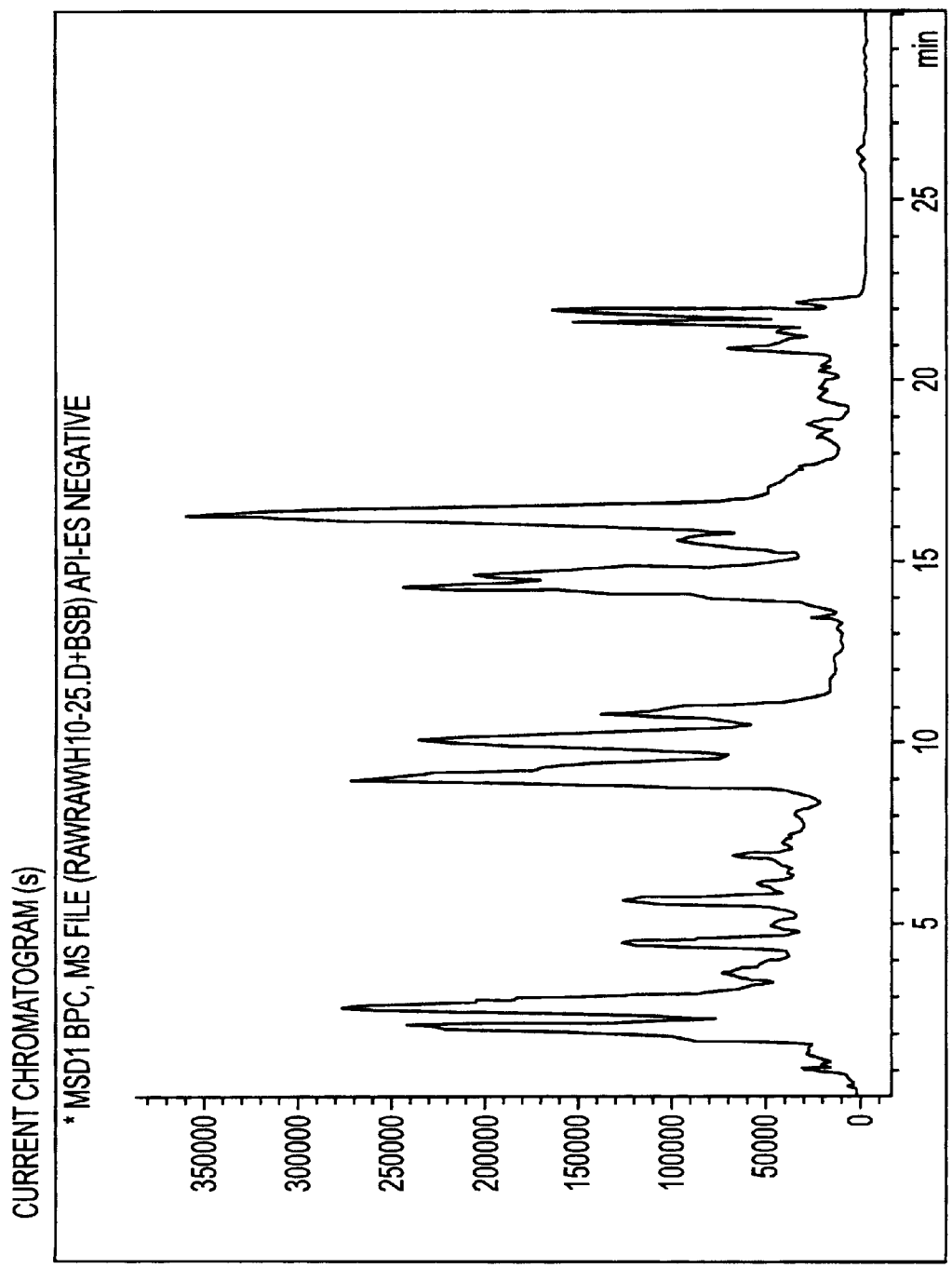
FIG. 11 is a LC/MS chromatogram of a pre-purified mixture of flavonoid and steroidal glycosides extract from Example 2.

The recorded LC/MS chromatogram of the pre-purified extract is presented in FIG. 11.

EXAMPLE 3

Figure 12:
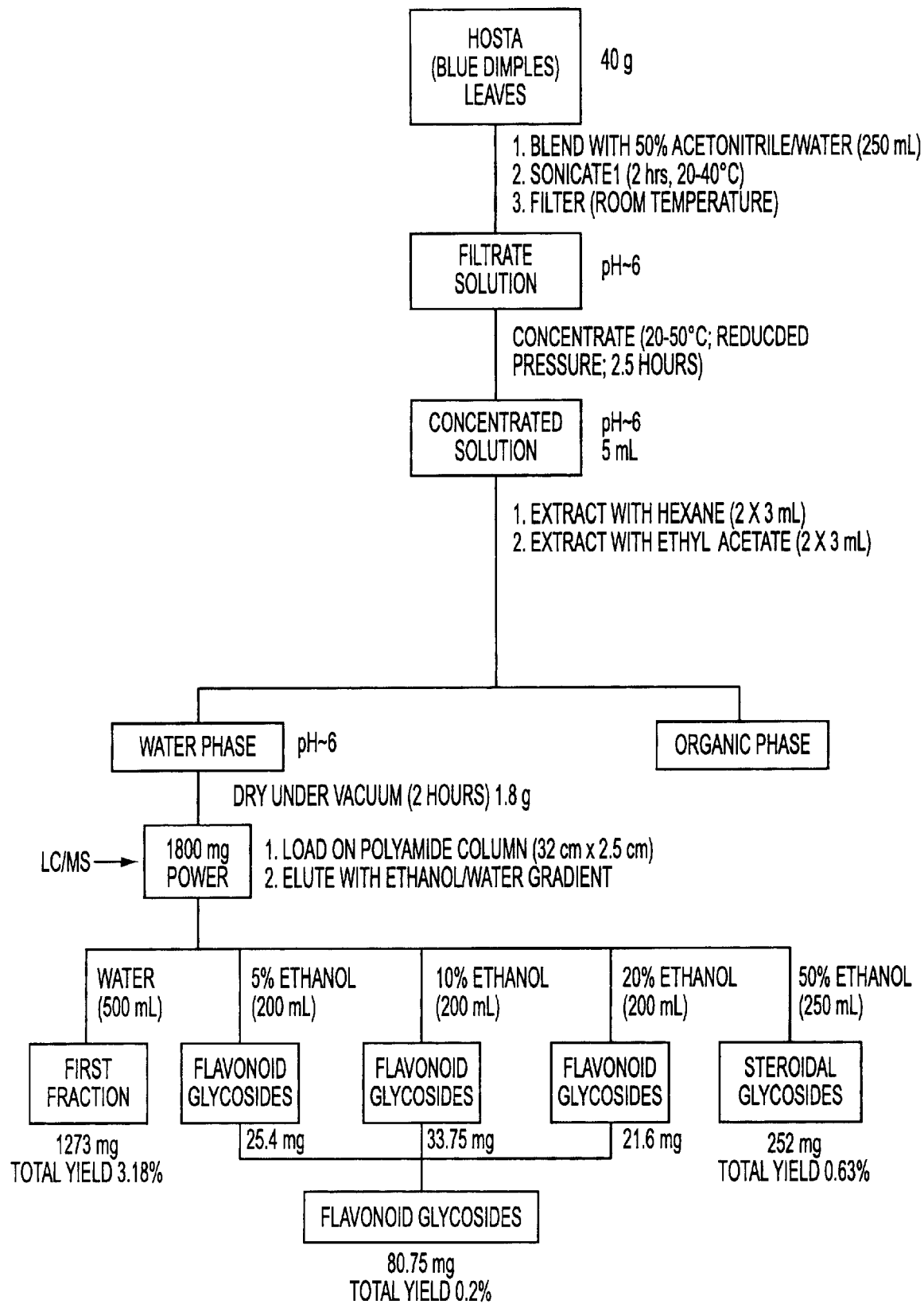
FIG. 12 is a graph which summarizes the procedure used for extraction, pre-purification and analyses of Hosta leaves in Example 3.

The procedure for extraction, pre-purification and analysis of Hosta leaves is depicted in FIG. 12. The fresh Hosta leaves (Blue Dimples) were hand picked in September. Fresh leaves (40 g) were chopped into small pieces and then ground in a blender with 50% acetonitrile solution in water (250 mL), followed by sonication for 2 hours at 20–40° C. The extract was filtrated to separate and remove fibrous material. The extract was concentrated to ca. 5 mL under reduced pressure on a Rotovapor. The concentrated solution was extracted twice with hexane (3 mL) followed by two-time extraction with ethyl acetate (3 mL). The aqueous phase was evaporated under vacuum to dryness to afford 1.8 g (4.5% yield) of the raw extract of flavonoid and steroidal glycosides in the form of powder. This powder (1.8 g) was dissolved in 10.0 mL of a mixture of water and acetonitrile (1:1) and subjected to HPLC/MS analysis.

The solution of this raw extract was separated by a column chromatography on polyamide resin (25 g, 80 mesh) with gradient elution of increasingly higher content of ethanol in water. The chromatography was monitored by HPLC/MSD/DAD. The first fraction eluted with water (500 mL) contained mainly some polar interfering compounds, such as sugars; the evaporation under vacuum to dryness yielded a solid powder (1273 mg). The second fraction was eluted with 5% ethanol-water solution (200 mL). The third fraction was eluted with 10% ethanol-water solution (200 mL) and the fourth fraction eluted with 20% ethanol-water solution (200 mL). The second, third and fourth fractions were combined and evaporated under vacuum to dryness to afford 80.75 mg (0.2% yield) of a crude mixture of flavonoid glycosides. The fifth fraction was eluted with 50% ethanol-water solution (250 mL). This fraction was evaporated separately under vacuum to dryness to afford 252 mg (0.63% yield) of a crude mixture of steroidal glycosides.

The HPLC/MSD/DAD analysis was performed with a system that consisted of an HPLC 1100 series LC/MSD (Hewlett-Packard) instrument, autoinjector, quaternary pump with on-line vacuum degassing unit, thermostated column compartment and diode array detector. At the same time, a mass detector was used. The API-EI mode was chosen. The negative ion mode provided better sensitivity and the interpretation of the spectra was found to be easier. So the analysis results were obtained in negative mode at fragmentation potential of 100 eV. A standard Zorbax C8 column (150 mm long×2.1 mm I.D.) with 5 µm particle size was used in these examples.

Figure 13:
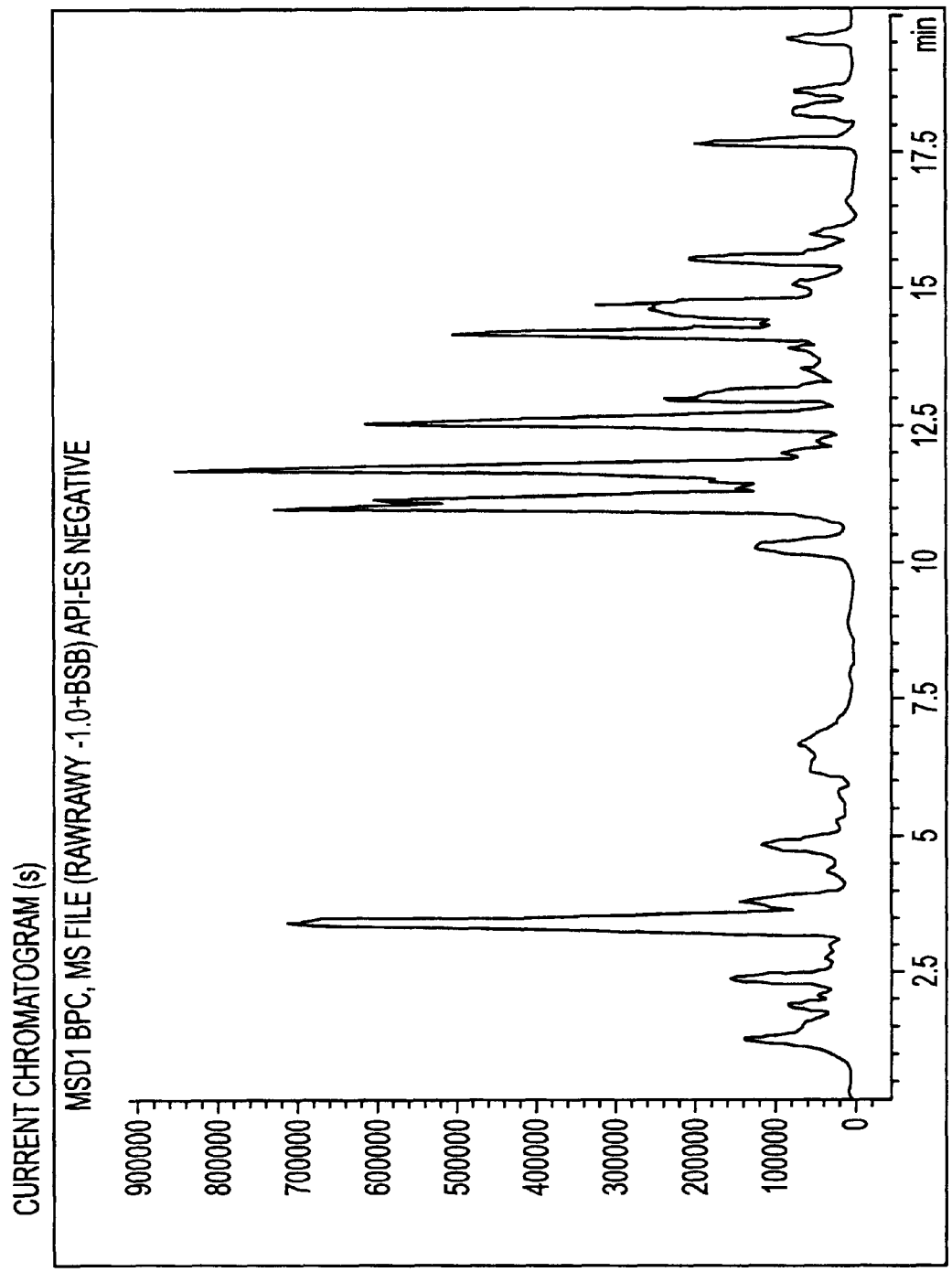
FIG. 13 is a LC/MS chromatogram of the raw extract from Example 3.

Operation conditions for the analysis were as follows:
Temperature 30° C.
Mobile phase consisted of an ACN/water mixture gradient:
0–6 minutes ACN 15%
6–18 minutes ACN from 15% to 90%
18–20 minutes ACN from 90% to 15%
The mobile phase flow rate was 0.4 mL/min.
Wavelength of UV detector was recorded on 280 nm.
The mass ion scan was from 100 to 1800.
The recorded LC/MS chromatogram of the raw extract is presented in FIG. 13.

REFERENCE CITED

U.S. Patent Documents

Ghai, G., et al, U.S. Pat. No. 5,955,269
Inada, S., et al., U.S. Pat. No. 4,968,787
Deninno, M. P., U.S. Pat. No. 5,698,526
Frazier, S. E., U.S. Pat. No. 4,238,483

Foreign Patent Documents

Ochi, M., et al., Steroid Saponin from Hosta and Antimicrobial and Antitumor Agents Containing It. JP 10 114, 791 [98 114,791] (C1. C07J71/00), May 6, 1998, application Ser. No. 96/270,292, Oct. 11, 1996; 12 pp; CA 129: 32293w Ochi, M., et al., Novel Steroidal Saponin and Antimicrobial Agents and Antitumor Agents Containing It. JP 10 158, 295 [98 158,295] (C1. C07J71), Jun. 16, 1998, application Ser. No. 96/320,142, Nov. 29, 1996; 12 pp; CA 129: 113511t.

Other Publications

Shibata, S., The Chemistry of Chinese Drugs. American Journal of Chinese Medicine (1979) 7(2): 103–141

Hartwell, J. L., et al., Antineoplastic Principles in Plants: Recent Developments in the Field. Advances in Pharmacology (1969) 1: 117–209

Rao, A. V., et al., Anticarcinogenic Effects of Saponins and Phytosterols. American Chemical Society Symposium Series (1997) 662: 313–324

Hartwell, J. L., Types of Anticancer Agents Isolated from Plants. Cancer Treatment Reports (1979) 60(8): 1031–1067

Hutabarat, L. S., et al., Development and Validation of an Isocratic High-Performance Liquid Chromatographic Method for Quantitative Determination of Phytoestrogens in Soya bean. Journal of Chromatography A (1998) 795: 377–382

Wolfender, J., et al., Comparison of Liquid Chromatography/Electrospray, Atmospheric Pressure Chemical Ionization, Thermospray and Continuous-flow Fast Atom Bombardment Mass Spectrometry for the Determination of Secondary Metabolites in Crude Plant Extracts. Journal of Mass Spectrometry and Rapid Communications in Mass Spectrometry (1995) (Special Issue): S35–S46

Maillard, M. P., et al., Use of Liquid Chromatography-Thermospray Mass Spectrometry in Phytochemical Analysis of Crude Plant Extracts. Journal of Chromatography (1993) 647: 147–154

Games, D. E., Combined High Performance Liquid Chromatography Mass Spectrometry. Biomedical Mass Spectrometry (1981) 8(9): 454–462

Vaccaro, W. D., et al., Sugar-Substituted 2-Azetidinone Cholesterol Absorption Inhibitors: Enhanced Potency by Modification of the Sugar. Bioorganic & Medicinal Chemistry Letters (1998) 8: 313–318

Price, K. R., et al., The Chemistry and Biological Significance of Saponins in Foods and Feedingstuffs. Critical Reviews in Food Science and Nutrition (1987) 26(1): 27–135

Fang, S., et al., Rapid Analysis of Steroidal Saponin Mixture Using Electrospray Ionization Mass Spectrometry Combined with Sequential Tandem Mass Spectrometry. Rapid Communications In Mass Spectrometry (1998) 12: 589–594

Maillard, M. P., et al., Determination of Saponins in Crude Plant Extracts by Liquid Chromatography-Thermospray Mass Spectrometry. Journal of Chromatography (1993) 647: 137–146

Lee, M., et al., Analysis of Saponins from Black Bean by Electrospray Ionization and Fast Atom Bombardment Tandem Mass Spectrometry. Journal of Mass Spectrometry (1999) 34: 804–812

Van Setten, D. C., et al., Multiple-Stage Tandem Mass Spectrometry for Structural Characterization of Saponins. Analytical Chemistry (1998) 70(20): 4401–4409

Hostettmann, K., et al., Saponins—Chemistry and Pharmacology of Natural Product, Cambridge University, Cambridge (1995)

Fuzzati, N., et al., Identification of Soyasaponins by Liquid Chromatography—Thermospray Mass Spectrometry. Journal of Chromatography A (1997) 777: 233–238

Mostad, H. B., et al., Separation and Characterization of Oleanene-type Pentacyclic Triterpenes from Gypsophila Arrostii by Liquid Chromatography-Mass Spectrometry. Journal of Chromatography (1987) 396: 157–168

Hardman, R., Board of Pharmaceutical Sciences (editor), Conception and Contraception, Exerpta Medica, Amsterdam, (1975) p. 60

Pietta, P., Flavonoids in Medicinal Plants. Antioxidant Health Dissertation (1998), 7 (Flavonoids in Health and Disease), 61–100

Pietta, P. G, et al., Fitomedicine e Nutrienti. Verona: Ricchiuto G M, (1996)

Bors, W., et al., Radical Chemistry of Flavonoid Antioxidants. Antioxidants in Therapy and Preventative Medicine (1990) 264: 165–170

Budzianowski, J., et al., Studies on Antioxidative Activity of Some C-glycosylflavones. Polish Journal of Pharmacology and Pharmacy (1991) 43: 395–401

Lonchampt, M. et al., Protective Effect of a Purified Flavonoid Fraction against Reactive Oxygen Radicals. Arzneimittelforschung (1989) 39(8): 882–885

Saija, A., et al., Flavonoids as Antioxidant Agents: Importance of their Interaction with Biomembranes. Free Radical Biology & Medicine (1995) 19(4): 481–486

Von Wacker, A., Antivirale Wirkung von Pflanzeninhaltsstoffen. Arzneimittelforschung (1978) 28(3): 347–350

Pietta, P. G, et al., Fitomedicine e Nutrienti. Verona: Ricchiuto G M, (1996)

Pathak, D., et al., Fitoterapia (1991) 62:371

Dawidar, A. M., et al., Mass Spectra of Steroid Saponins. Journal of Pharmaceutical Sciences (1974) 63: 140–142

Harborn and Williams. The Flavonoids. Ed. Harborn, J. B., et al., Chapman and Hall, (1975): 376–441

Franski, R., et al., Application of Mass Spectrometry to Structural Identification of Flavonoid Monoglycosides Isolated from Shoot of Lupin (Lupinus Luteus L.). Acta Biochimica Polonica (1999) 46(2): 459–478

Nakaori, T., et al, Journal of Pharmaceutical Sciences Japan. (1956) 76: 323 Lunte, S. M., Structural Classification of Flavonoids in Beverages by Liquid Chromatography With Ultraviolet-visible and Electrochemical Detection. Journal of Chromatography (1987) 384: 371–382

Tsuchiya, H., High-performance Liquid Chromatographic Analysis of Polyhydroxyflavones Using Solid-phase Borate-complex Extraction. Journal of Chromatography B (1998) 720: 225–230

Guinaudeau, H., et al., Phytochemistry (1981) 20: 1113

Hosny, M., Novel Isoflavone, Cinnamic Acid, and Triterpenoid Glycosides in Soybean Molasses. Journal of Natural Products (1999) 62(6): 853–858

Harborn, J. B. et al, Flavone and Flavonol Glycosides. Flavonoids: Advances in Research (1982) 261–311. Editor: Harborne, J.

Wolf, W. J., et al, Journal of American Oil Chemists Society. (1970) 47: 89 Stewart, et al., Biochemical Systems Ecology. (1980) 8: 119

Galensa, R., et al, Analyse von Flavonoidglycosiden durch Hochdruck-Flusskeits-Chromatographie. (1978) 166: 355–358

Domon, B., Journal of Chromatography (1984) 315: 441

Hasler, A., et al., High-performance Liquid Chromatographic Determination of Five Widespread Flavonoid Aglycones. Journal of Chromatography (1990) 508: 236–240 39th Annual Congress on Medicinal Plant Research September 1991

Iida, J., et al., Application of Thermospray Liquid Chromatography/mass Spectrometry to Analysis of Glycosides. Analytical Sciences (1991) (Supplement): 963–966

Maillard, M. P., et al., Thermospray LC-MS Analysis of Saponins in Crude Plant Extracts. Planta Medica (1992) 58 (Supplement Issue 1): A 673

Wolfender, J. L., et al., Liquid Chromatographic-Thermospray Mass Spectrometric Analysis of Crude Plant Extracts Containing Phenolic and Terpene Glycosides. Journal of Chromatography (1993) 647: 183–190

Pietta, P., et al., Thermospray Liquid Chromatography-mass Spectrometry of Flavonol Glycosides From Medicinal Plants. Journal of Chromatography A (1994) 661: 121–126

Wolfender, J. L., et al., Liquid Chromatography Combined with Thermospray and Continuous-flow Fast Atom Bombardment Mass Spectrometry of Glycosides in Crude Plant Extracts. Journal of Chromatography A (1995) 712: 155–168

Hakkinen, S., et al., High-performance Liquid Chromatography with Electrospray Ionization Mass Spectrometry and Diode Array Ultraviolet Detection in the Identification of Flavonol Aglycones and Glycosides in Berries. Journal of Chromatography A (1998) 829: 91–100

Schopke, T., et al., Application of MS-MS for the Rapid, Comparative Analysis of Saponin Mixtures as Exemplified by the Deacylated and Partially Deacylated Triterpenoid Saponins of Bellis Annua. Planta Medica (1996) 62: 336–340

Mauri, P. L., et al., Liquid Chromatography/Electrospray Ionization Mass Spectrometric Characterization of Flavonol Glycosides in Tomato Extracts and Human Plasma. Rapid Communications in Mass Spectrometry (1999) 13: 924–931

Stobiecki, M., et al., Detection of Isoflavonoids and their Glycosides by Liquid Chromatography/Electrospray Ionization Mass Spectrometry in Root Extracts of Lupin (Lupinus Albus). Pytochemical Analysis (1999) 10: 198–207

Gelpi, E., Biomedical and Biochemical Applications of Liquid Chromatography-Mass Spectrometry. Journal of Chromatography A (1995) 703:59–80

Watson, D. G., et al., Analysis of Flavonoids in Tablets and Urine by Gas Chromatography/Mass Spectrometry and Liquid Chromatography/Mass Spectrometry. Rapid Communications in Mass Spectrometry (1998) 12: 153–156

Justesen, U., et al., Quantitative Analysis of Flavonols, Flavones, and Flavanones in Fruits, Vegetables and Beverages by High-performance Liquid Chromatography with Photo-diode Array and Mass Spectrometric Detection. Journal of Chromatography (1998) 799: 101–110

Jiang Su New Medical College (ed.), "Dictionary of Traditional Chinese Crude Drugs"', vol.1, Shanghai Scientific Technologic Publishers, Shanghai, (1977), p.557

Budzianowski, J., Kaempferol Glycosides from Hosta Ventricosa. Phytochemistry (1990) 29(1): 3463–3467

Takeda, K., et al., Studies on the Steroidal Components of Domestic Plants—XLVI Constituents of Hosta Species (3) $\Delta 25(27)$-Sapogenins. Tetrahedron, (1965) 21: 2089–2093

Takeda, K., et al., Studies on Biochemical Transformation of Plant Steroids. Part Biochemical Interconversion of the Δ25(27)- and the Saturated 25D- or 25L-Sapogenins. Journal of Chemical Society C (1967) (9): 876–882

Takeda, K., et al., Studies on Biochemical Transformation of Plant Steroids. Part II. Biochemical Conversion of Gitogen into 12-Oxygenated Sapogenins in Hosta Kiyosumiensis. Chemical and Pharmaceutical Bulletin (1968) 16(2): 275–279

Mimaki, Y., et al., Steroidal Saponins from the Underground Parts of Hosta Longpipes and Their Inhibitory Activity on Tumor Promoter-Induced Phospholipid Metabolism. Chemical and Pharmaceutical Bulletin (1995) 43(7): 1190–1196

Mimaki, Y., et al., Steroidal Saponins from Hosta Longpipes and Their Inhibitory Activity on Tumor Promoter-Induced Phospholipid Metabolism of HeLa Cells. Phytochemistry (1996) 42(4): 1065–1070

Mimaki, Y., et al., Steroidal Glycosides from the Underground Parts of Hosta Plantaginea Var. Japonica and Their Cytostatic Activity on Leukemia HL-60 Cells. Phytochemistry (1997) 44(2): 305–310

Mimaki, Y., et al., Steroidal Saponins from the Rhizomes of Hosta Sieboldii and Their Cytostatic Activity On HL-60 Cells. Phytochemistry (1998) 48(8): 1361–1369

What is claimed is:

1. A method of analytically determining and characterizing Hosta flavonoid glycosides and Hosta steroidal glycosides comprising the following steps:
    (a) obtaining a sample to be analyzed;
    (b) preparing said sample to be analyzed;
    (c) mixing said sample with aqueous polar solvents to make a crude extract;
    (d) pre-purifying said crude extract to remove interfering components;
    (e) isolating said Hosta flavonoid glycosides and Hosta steroidal glycosides through actively guided fractionation; and
    (f) analyzing and simultaneously identifying said Hosta flavonoid glycosides and Hosta steroidal glycosides by use of High Pressure Liquid Chromatography (HPLC) combined with Electrospray Ionization Mass Spectrometry and Diode Array Ultra-Violet and Visible Spectroscopy detection techniques.

2. The method of claim 1 wherein the sample is selected from the group consisting of polar phytochemicals.

3. The method of claim 2 wherein said polar phytochemicals are Hosta flavonoid glycosides and Hosta steroidal glycoside compounds.

4. The method of claim 3 wherein said compounds are selected from the group consisting of a naturally occurring biological material, nutraceutical formulations, synthetic complex mixtures or combinations thereof.

5. The method of claim 4 wherein said naturally occurring biological material is selected from the group consisting of Hosta plants or Hosta herbs.

6. The method of claim 4 wherein said Hosta nutraceutical formulations are selected from the group consisting of powders, solutions, tinctures, suspensions, syrups, capsules and tablets.

7. The method of claim 1 wherein said sample preparation step occurs by blending, or crushing said sample.

8. The method of claim 1 wherein said polar solvent is selected from the group consisting of pure water and low molecular weight alcohols, ketones, and acetonitrile.

9. The method of claim 8 wherein said low molecular weight alcohols are selected from the group consisting of n-propanol and iso-propane.

10. The method of claim 1 wherein said mixing step occurs by sonication.

11. The method of claim 1 wherein said pre-purification occurs by precipitation through concentrating the crude extract volume.

12. The method of claim 1 wherein said pre-purification occurs by precipitation through refrigeration of the crude extracts to below 4° C.

13. The method of claim 1 wherein said pre-purification occurs by precipitation through concentrating the crude extract volume and refrigeration to below 4° C.

14. The method of claim 1 wherein said pre-purification from non-polar interfering components occurs by subjecting said crude extract to a liquid-liquid extraction with water immiscible organic solvent.

15. The method of claim 12 wherein said pre-purification occurs by defatting said crude extract by liquid-liquid extraction with water immiscible organic solvent.

16. The method of claim 14 wherein said immiscible organic solvent is selected from the group consisting of alkanes, cycloalkanes, ethers and lower esters.

17. The method of claim 16 wherein said lower esters are selected from the group consisting of methyl acetate, propyl acetate and methyl propionate.

18. The method of claim 15 wherein said immiscible organic solvent is selected from the group consisting of alkanes and cycloalkanes.

19. The method of claim 1 wherein said pre-purification from polar interfering components occurs by subjecting said crude extract to open column or flash column chromatography using polyamide resins or weakly acidic cation exchange resins as the solid phase and using mixtures of water and polar solvents as the mobile phase.

20. The method of claim 19 wherein said polar solvents are selected from the group consisting of water, alcohols, ketones and acetonitrile.

21. The method of claim 19 wherein said weakly acidic cation exchange resin characterized by a plurality of active carboxylic groups.

22. A method of analytically determining and characterizing Hosta flavonoid glycosides and Hosta steroidal glycosides comprising the following steps:
    a) obtaining a sample to be analyzed;
    b) preparing said sample to be analyzed;
    c) mixing said sample with aqueous polar solvents to make a crude extract;
    d) pre-purifying said crude extract to remove interfering components;
    e) isolating said Hosta flavonoid glycosides and Hosta steroidal glycosides through actively guided fractionation; and
    f) analyzing and identifying said Hosta flavonoid glycosides and Hosta steroidal glycosides.

23. The method of claim 22 wherein the analysis occurs by actively guided fractionation of said Hosta flavonoid glycosides and Hosta steroidal glycosides.

24. The method of claim 22 wherein said actively guided fractionation of said Hosta flavonoid glycosides and Hosta steroidal glycosides is accomplished by the application of Reverse Phase HPLC.

25. The method of claim 22 wherein said analysis and simultaneous identification occurs by use of Reversed Phase High Pressure Liquid Chromatography (HPLC) combined with Electrospray Ionization Mass Spectrometry and Diode Array Ultra-Violet and Visible Spectroscopy detection techniques.

26. The method of claim 25 wherein said Electrospray Mass Spectrometry technique is used for the detection of thermally liable compounds and prevents the creation of artifacts.

27. The method of claim 26 wherein said Electrospray Ionization Mass Spectrometry detection technique is operated in the negative ion mode.

28. The method of claim 27 wherein said analysis further includes the post-column application of triethylamine to enhance the sensitivity of the Electrospray Ionization Mass Spectrometry detection technique.

29. The method of claim 1 wherein said detection techniques allow for the selective and simultaneous identification of individual Hosta flavonoid glycoside and Hosta steroidal glycoside components contained in said pre-purified extract.

30. The method of claim 1 wherein said analysis yields information which includes molecular weight, number and type of glycoside substituents, and mode of differentiation between the different types of aglycones present in the components of said Hosta extract.

* * * * *